US011241166B1

(12) United States Patent
Lee

(10) Patent No.: US 11,241,166 B1
(45) Date of Patent: Feb. 8, 2022

(54) COMMUNICATIONS BETWEEN SMART CONTACT LENS AND INGESTIBLE SMART PILL

(71) Applicant: Verily Life Sciences LLC, Mountain View, CA (US)

(72) Inventor: Shungneng Lee, Sunnyvale, CA (US)

(73) Assignee: Verily Life Sciences, LLC, Mountain View, CA (US)

( * ) Notice: Subject to any disclaimer, the term of this patent is extended or adjusted under 35 U.S.C. 154(b) by 1049 days.

(21) Appl. No.: 15/393,767

(22) Filed: Dec. 29, 2016

Related U.S. Application Data

(60) Provisional application No. 62/290,757, filed on Feb. 3, 2016.

(51) Int. Cl.
*A61B 5/00* (2006.01)
*A61B 3/113* (2006.01)
(Continued)

(52) U.S. Cl.
CPC .............. *A61B 5/073* (2013.01); *A61B 3/113* (2013.01); *A61B 5/0024* (2013.01);
(Continued)

(58) Field of Classification Search
CPC ... A61B 5/073; A61B 5/14532; A61B 5/0024; A61B 5/4839; A61B 5/6861;
(Continued)

(56) References Cited

U.S. PATENT DOCUMENTS 4,494,950 A * 1/1985 Fischell ............... A61B 5/0002 604/66
7,978,064 B2 7/2011 Zdeblick et al.
(Continued)

FOREIGN PATENT DOCUMENTS

CA 2922864 A1 * 3/2015

OTHER PUBLICATIONS

Comstock, J., "FDA expands Proteus Digital Health's clearance to include measuring medication adherence," http://mobihealthnews.com/44949/fda-expands-proteus-digital-healths-clearance-to-include-measuring-medication-adherence (2015).
(Continued)

*Primary Examiner* — Jacqueline Cheng
*Assistant Examiner* — Tho Q Tran
(74) *Attorney, Agent, or Firm* — McDonnell Boehnen Hulbert & Berghoff LLP

(57) ABSTRACT

A body-mountable device is provided to facilitate communication, via in-body electrical signals transmitted via electrodes of the body-mountable device into fluid of the body, with a smart pill located in a gastrointestinal tract of a body to which the body-mountable device is mounted or with some other device located within the body. The body-mountable device can be a contact lens or other eye-mountable device such that the electrodes of the eye-mountable device can transmit in-body electrical signals via tear fluid. The body-mountable device could transmit a command to the smart pill to dispense a drug into the body. The smart pill could transmit, via in-body electrical signals, an indication of a detected property of the gastrointestinal tract to the body-mountable device. A latency of transmission of signals between the body-mountable device and the smart pill could be used to determine the location of the smart pill within the gastrointestinal tract.

19 Claims, 6 Drawing Sheets

(51) Int. Cl.
  *A61F 9/00* (2006.01)
  *A61B 5/07* (2006.01)
  *A61B 5/145* (2006.01)
  *A61B 5/1473* (2006.01)

(52) U.S. Cl.
  CPC .......... *A61B 5/0031* (2013.01); *A61B 5/1473* (2013.01); *A61B 5/14532* (2013.01); *A61B 5/14539* (2013.01); *A61B 5/4839* (2013.01); *A61B 5/6821* (2013.01); *A61B 5/6861* (2013.01); *A61F 9/0017* (2013.01)

(58) Field of Classification Search
  CPC ... A61B 5/6821; A61B 5/1473; A61B 5/0031; A61B 9/0017; A61B 5/14539; A61B 3/113; A61B 5/053; A61M 60/878; A61M 2205/3507; A61M 2205/3538
  See application file for complete search history.

(56) References Cited

U.S. PATENT DOCUMENTS

| | | | | |
|---|---|---|---|---|
| 8,932,221 | B2 * | 1/2015 | Colliou | A61B 5/0031 600/302 |
| 2002/0049389 | A1 * | 4/2002 | Abreu | A61B 5/412 600/558 |
| 2002/0099423 | A1 * | 7/2002 | Berg | A61N 1/3727 607/60 |
| 2002/0143326 | A1 * | 10/2002 | Foley | A61B 18/1492 606/41 |
| 2009/0137883 | A1 * | 5/2009 | Chiba | A61B 1/041 600/302 |
| 2009/0270032 | A1 * | 10/2009 | Kassayan | H04B 5/0025 455/41.1 |
| 2009/0281387 | A1 * | 11/2009 | Takizawa | A61B 1/00082 600/117 |
| 2011/0028807 | A1 * | 2/2011 | Abreu | A61B 3/1241 600/321 |
| 2013/0022175 | A1 * | 1/2013 | Abramovich | A61B 6/145 378/189 |
| 2015/0343144 | A1 * | 12/2015 | Altschul | A61B 5/0022 604/503 |
| 2016/0158534 | A1 * | 6/2016 | Guarraia | A61N 1/0548 607/134 |
| 2017/0079771 | A1 * | 3/2017 | Roholt | G02C 7/04 |

OTHER PUBLICATIONS

Hackworth, Steven Andrew. Design, optimization, and implementation of a volume conduction energy transfer platform tor implantable devices, University of Pittsburgh, 2010.

Hafezi, H., et al. "An ingestible sensor for measuring medication adherence." Biomedical Engineering, IEEE Transactions, vol. 62, No. 1, p. 99-109 (2015).

Stanford engineer invents safe way to transfer energy to medical chips in the body, http://news.stanford.edu/news/2014/may/electronic-wireless-transfer-051914.html (2014).

Zhu, W., et al. "Volume conduction energy transfer for implantable devices." Journal of biomedical research, vol. 27, No. 6, p. 509-514 (2013).

* cited by examiner

US 11,241,166 B1

COMMUNICATIONS BETWEEN SMART CONTACT LENS AND INGESTIBLE SMART PILL

CROSS-REFERENCE TO RELATED APPLICATION

This application claims priority to U.S. Provisional Patent Application No. 62/290,757, filed Feb. 3, 2016, which is hereby incorporated by reference in its entirety.

BACKGROUND

Unless otherwise indicated herein, the materials described in this section are not prior art to the claims in this application and are not admitted to be prior art by inclusion in this section.

A variety of physiological parameters of a human body can be detected and used to determine a health state or other information about the body (e.g., to determine a property of contents of the gastrointestinal tract of the body, to determine that the body is in danger from an adverse health state) and/or to perform some activities relating to the body (e.g., to inform a drug dosage, to decide a course of medical treatment, to adjust an athletic training regimen). Such physiological parameters can be detecting at a plurality of points in time and/or at a number of different locations within the gastrointestinal tract by ingestible devices (e.g., devices having a shape and size similar to a pill) that include sensors (e.g., cameras) and other electronic components configured to measure one or more physiological parameters and/or to perform some other functions, e.g., to log and/or record measured physiological parameters, or to perform some other function. Such ingestible devices can be powered by on-board batteries, or some other power source. Such ingestible devices can be collected following excretion, e.g., to allow access to data logged in a memory of the ingestible devices. Additionally of alternatively, such ingestible devices could operate to transmit signals (e.g., to transmit radio-frequency signals) form within the gastrointestinal tract to devices located outside of the body.

SUMMARY

Some embodiments of the present disclosure provide a system including: (i) a first device that is mountable on an external body surface and that includes a plurality of first-device electrodes and a first-device transmitter coupled to the plurality of first-device electrodes; and (ii) a second device that is operable in a gastro-intestinal (GI) tract and that includes a plurality of second-device electrodes and a second-device receiver coupled to the plurality of second-device electrodes. The first-device transmitter is operable to transmit an in-body electrical signal via the first-device electrodes and the second-device receiver is operable to receive, via the second-device electrodes, the in-body electrical signal transmitted by the first-device transmitter when the first device is mounted on the external body surface such that the plurality of first-device electrodes are in contact with fluid of the body and the second device is in the GI tract.

Some embodiments of the present disclosure provide a body-mountable device that includes: (i) a plurality of electrodes; and (ii) a transmitter coupled to the plurality of electrodes. The transmitter is operable to transmit, via the electrodes, an in-body electrical signal that can propagate through the body to be received by a second device when the body-mountable device is mounted on an external body surface such that the plurality of electrodes are in contact with fluid of the body and the second device is in a gastro-intestinal (GI) tract.

Some embodiments of the present disclosure provide a method including: (i) transmitting an in-body electrical signal via a plurality of first-device electrodes of a first device that is mounted to an external body surface of a body such that that the plurality of first-device electrodes are in contact with fluid of the body; and (ii) receiving, via a plurality of second-device electrodes of a second device that is in a gastro-intestinal (GI) tract, the in-body electrical signal transmitted via the first-device electrodes.

These as well as other aspects, advantages, and alternatives, will become apparent to those of ordinary skill in the art by reading the following detailed description, with reference where appropriate to the accompanying drawings.

DETAILED DESCRIPTION

Figure 1:
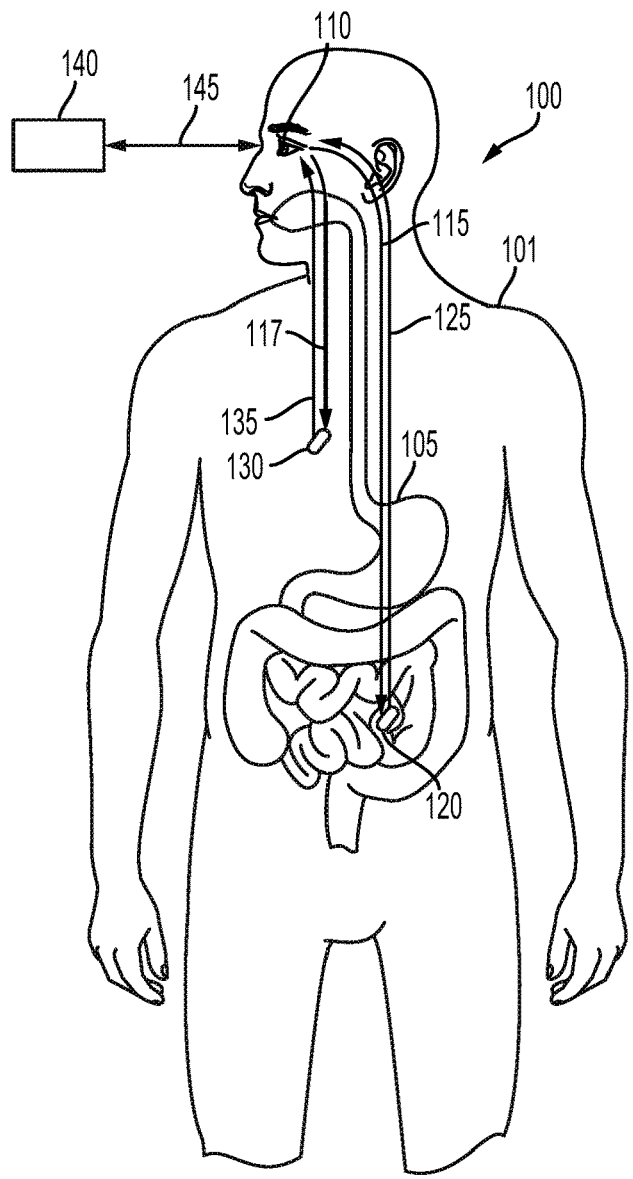
FIG. 1 is a schematic of devices that are configured to communicate via transmission of in-body electrical signals.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Due to the electronic properties of the tissues of the human (or animal) body, it can be difficult to communicate with devices located within the body (e.g., implanted sensors, implanted stimulators, injected electronic sensor platforms, or other implanted or ingested devices). Tissues of the body can attenuate high-frequency electromagnetic waves (e.g., radio frequency electromagnetic waves). Conversely, while lower-frequency electromagnetic waves may be less attenuated by the tissues of the body, the sizes of antennas or other transmission or reception elements necessary to facilitate such low-frequency electromagnetic communication are incompatible with functional constraints on the size of implanted and/or ingested devices.

As an alternative, communication between devices within a body, or in electrical contact with fluids of a body, can be provided by the transmission and reception of in-body electrical signals. Such in-body electrical signals include time-varying electrical fields that propagate through the body (e.g., via ionic conduction through the low-conductivity interstitial fluids, intracellular fluids, blood, or other low-conductivity fluids or tissues of the body). Such in-body electrical signals can be generated by injecting a time-varying current through two or more electrodes that are in contact with fluid of the body (e.g., with tear fluid of an eye, with blood or interstitial fluid within a tissue, with chyme or other digestive fluids within a gastrointestinal (GI) tract). Such in-body electrical signals can be detected by detecting the potential between two or more electrodes that are in contact with fluid of the body. Note that it is possible to transmit and/or receive such in-body electrical signals via the skin surface; however, such transmission may be significantly attenuated, e.g., by the high impedance of the stratum corneum or other low-conductivity elements of the skin.

Communication, using such in-body electrical signals, could be provided by generating a plurality of pulses or other time-varying signals via two or more electrodes that are in contact with a fluid of the body. This could include generating a plurality of pulses (e.g., current pulses through the electrodes and/or voltage pulses applied across the electrodes). A timing, polarity, pulse width, amplitude, or other properties of the pulses could be modulated to indicate information (e.g., to indicate commands, sensor readings, program updates). Such pulses could be modulated according to a variety of encoding schemes, e.g., according to a pulse position encoding, a Manchester encoding, or some other code or communications protocol.

In order to facilitate communication, using such in-body electrical signals, with devices located within the body, a body-mountable device could be provided to generate in-body electrical signals and/or to detect in-body electrical signals. Such a body-mountable device could include two or more electrodes that are in contact with fluids of the body (e.g., interstitial fluid of a subcutaneous tissue, tear fluid of an eye) when the device is mounted to the external body surface. In some examples, the body-mountable device could be mountable to a skin surface and include penetrating electrodes configured to pierce the skin or to otherwise access interstitial fluids beneath the surface of the skin or to otherwise contact fluids of the body with the electrodes. In other examples, such a body-mountable device could be a contact lens or other eye-mountable device that includes two or more electrodes that are in contact with tear fluid of the eye when the device is mounted to the eye and/or when an eyelid is closed over the eye (e.g., the electrodes could be directed away from the surface of the eye when the device is mounted to the eye).

Electrodes of such body-mountable devices could be used to produce in-body electrical signals (e.g., by injecting pulses of current through the electrodes) and/or to detect in-body electrical signals (e.g., by detecting time-varying patterns of electrical potential across the electrodes). Such a body-mountable device could act as a bridge to facilitate communication between devices located within the body (e.g., an ingestible smart pill) and devices located outside of the body (e.g., a cellphone, a computer, a tablet) via optical, radio frequency, or some other means of wireless communications. Additionally or alternatively, the body-mountable device could act as a user interface for devices within the body, receiving commands from a user (e.g., by detecting specified patterns of eye blinks) and/or providing indications to the user (e.g., by emitting a light toward the retina of a wearer).

In some examples, such a body-mountable device could facilitate communications with an ingestible smart pill. This could include receiving, via in-body electrical signals generated by the smart pill, indications of a property of the GI tract and/or of the body that are detected by the smart pill using a sensor of the smart pill (e.g., an analyte sensor, a camera, a pH sensor). Additionally or alternatively, the body-mountable device could send commands to the smart pill, e.g., to perform a measurement using a sensor of the smart pill or to release a quantity of a drug from the smart pill. Additionally or alternatively, such a body-mountable device could communicate, via in-body electrical signals, with other devices within the body (e.g., implanted devices, subcutaneous device, devices located in the bloodstream of the body).

Transmission and reception of in-body electrical signals could facilitate additional applications. In some examples, a latency between transmission of an in-body electrical signal by a body-mountable device and reception, by the body-mountable device, of an in-body electrical signal emitted by a smart pill in response to the signal emitted by the body-mountable device could be used to determine a distance between the body-mountable device and the smart pill. Such a determination could be based on a speed of propagation of in-body electrical signals (e.g., related to an average conductivity of tissues and/or fluids of the body). The determined distance between the smart pill and the body-mountable device could be used to determine where, within the GI tract, the smart pill is located. Such a determination could be used to time the administration of a drug by the smart pill, e.g., such that the drug is delivered to a specified portion of the GI tract and not to other portions of the GI tract. Additionally or alternatively, such a determination could be used to time the operation of a sensor of the smart pill and/or to tag sensor readings generated by the smart pill with information about the location of the smart pill when the sensor readings were generated.

II. Communication Between Devices Via In-Body Electrical Signals

It can be difficult to communicate between devices that are disposed within a human (or animal) body. The electrical properties (e.g., conductivity) of tissues and fluids of the body can act to attenuate, distort, or otherwise alter high-frequency electromagnetic waves (e.g., radio frequency waves) emitted by a device located within the body and/or to distort such waves emitted from a device located outside the body to a device located within the body. Lower-frequency waves may be used to transmit information through the tissue of the body, but the transmission and/or reception of such waves may require large antennas or other components that may not be compatible with applications of a device (e.g., may not be compatible with the device being ingestible, able to be disposed within a gastrointestinal (GI) tract, or having a small size).

In-body electrical signals could be used to facilitate communication between devices disposed within a body and/or between such devices and devices in contact with an external surface of the body. In-body electrical signals can include time-varying patterns of current and/or voltage that can propagate through tissues and/or fluids of the body, e.g., via ionic conduction within the tissues and/or fluids of the body. For example, in-body electrical signals could be generated by injecting a time-varying current (e.g., one or more pulses of current) through two electrodes that are in contact with a fluid and/or tissue of a body and that are separated by a distance. Such contact can be provided by placing the electrodes in contact with an externally accessible fluid of the body, e.g., tear fluid of the eye or saliva of the mouth. Additionally or alternatively, the electrodes could penetrate skin (or other tissue of an external body surface) to contact interstitial fluid beneath the skin (e.g., by being configured to pierce the stratum corneum of the skin, or by penetrating through punctures formed by some other device, e.g., by a lancet).

Injection of the time-varying current can cause a pattern of time varying-currents and/or voltages to propagate through the body from the electrodes, e.g., as a substantially dipolar, time-dependent field with an origin centered on the electrodes. Such a generated in-body electrical signal can then be detected using two or more electrodes of a further device to detect changes in the voltage between the two or more electrodes over time.

In-body electric signals (e.g., time-varying patterns of current and/or voltage related to the injection of pulses or other time-varying currents through electrodes into fluids or tissues of a body) could propagate through the body over time in a variety of ways related to the electrical properties of the tissues and/or fluids of the body, the geometry of such tissues and/or of the body, or other properties of the body. Such signals could propagate away from a device that has generated the signals at a specified rate, e.g., at a rate related to the conductivity of tissues and fluids of the body. Further, as the in-body electrical signals propagate away from a generating device, the signals may be reduced in magnitude (e.g., a magnitude of a voltage gradient of the signals could be reduces), waveform shape (e.g., a pulse in the signals could spread as the signals propagate), or with regard to some other property. Such changes in the in-body electrical signals could be related to spreading of the energy of the signals across volumes of the body, absorption of energy of the in-body electrical signals by tissues or fluids of the body (e.g., via ohmic heating), multipath effects, or other processes related to the propagation of time-varying patterns of current and/or voltage within tissues and/or fluids of a body.

The shape, pulse width, or other properties of a wavefront or other temporal or spatial feature of an in-body electrical signal can be related to the relative locations of electrodes used to generate the in-body electrical signal and the means by which the electrodes are used to generate the in-body electrical signal. For example, more than two electrodes could be driven with respective current and/or voltage waveforms, e.g., in order to control a direction of a beam of in-body electrical signals transmitted from a first device that includes the more than two electrodes. Increasing a distance between two electrodes that are used to generate in-body electrical signals could increase a dipole moment and/or characteristic size of a dipolar electrical field of the generated in-body electrical signals. Conversely, the relative locations or other properties of electrodes used to detect in-body electrical signals could be specified to facilitate detection of the in-body electrical signals (e.g., by increasing a distance between such electrodes to enable detection of differences in electrical potential between more distant locations in a body, by operating a number of electrodes as a phased array in order to detect in-body electrical signals from one or more specified direction relative to a device that includes the electrodes).

The transmission and reception of in-body electrical signals (e.g., by different devices located on or within a body and that each include two or more electrodes in electrical contact within tissues and/or fluids of the body) could facilitate communications between different devices located on or within the body and/or could facilitate other functionality, e.g., determining a distance between and/or relative location of such devices on or within the body. FIG. 1 illustrates a system of devices 100 located on or within a body 101. The system includes an eye-mountable device 110 mounted to an eye (e.g., on the surface of a cornea of the eye) of the body 101, an ingestible device (e.g., a smart pill) 120 located within a gastrointestinal (GI) tract 105 of the body 101, and a further device 130 located within the body 101 (e.g., implanted within a tissue of the body, located within the bloodstream of the body). An external system 140 (e.g., a cellphone, a tablet, a computer, a server, an insulin pump) is provided and is operable to communicate with the eye-mountable device 110, e.g., via optical or radio frequency wireless transmissions 145.

By being mounted to the eye of the body 101, the eye-mountable device 110 can generate and/or receive in-body electrical signals (e.g., to 115 and/or from 125 the ingestible device 120 or to 117 and/or from 135 the further device 130) via the tear fluid of the eye, which is in electrical contact (e.g., via ionic conduction) with further tissues and/or fluids of the body 101. Such an electrical connection to the tissues and/or fluids of the body 101 may be lower-impedance or otherwise improved compared to a connection to the tissues and/or fluids of the body via the skin (e.g., using electrodes of a body-mountable device that is mounted such that the electrodes are in contact with the skin of the body). Further, by being located on the surface of the body 101, the eye-mountable device 110 can communicate wirelessly (e.g., via optical or radio frequency wireless signals) with systems located outside of the body (e.g., with external system 140). Thus, the eye-mountable device 110 could serve as a bridge between devices outside of the body (e.g., cellphones, tablets, servers) and devices inside the body (e.g., implanted devices, ingested devices, devices within the bloodstream), allowing information and commands to be passed between devices outside of the body and devices inside of the body.

Note that the eye-mountable devices described herein (e.g., 110, 310, 510) are used to illustrate by example a broader class of body-mountable devices that may be configured and operated to send and/or receive in-body electrical signals via electrodes that are in contact with fluids of a body when the body-mountable device is mounted to an external body surface of the body. In examples wherein the body-mountable device is an eye-mountable device (e.g., as in FIGS. 1, 3A, 3B, 3C, 3D, 5), the external body surface can be a corneal surface of an eye, and the fluid can be a tear fluid of the eye. In other examples, the body-mountable device could be mountable to some other external body surface such that the electrodes can access some other body fluid that is accessible from outside of the body. For example, the body-mountable device could be mountable to an external body surface within the mouth of a body (e.g., to a gingival surface, to a palatal surface, to a sublingual surface) and the fluid can be saliva of the mouth. Additionally or alternatively, a body-mountable device could be configured to penetrate the external body surface to access fluid beneath or within the tissue of the body surface, e.g., to penetrate the stratum corneum of skin to access blood, interstitial fluid, or other fluids beneath the stratum corneum. In such examples, the electrodes could be sharpened or otherwise configured to pierce the external body surface (e.g., to pierce the skin to place the ends of the electrodes in contact with subcutaneous interstitial fluid). Alternatively, punctures or other features could be formed through the skin by a lancet or some other means, and the electrodes of the body-mountable device could penetrate the skin via the formed punctures or other features in the skin.

In-body electrical signals, as described herein, propagate at a finite rate through tissues and fluids of a body. This rate can be related to a degree of conductivity of the tissues and fluids of the body. Thus, if the conductivity and/or rate of propagation of the in-body electrical signals is known and/or measured, a distance, within the body 101, between devices (e.g., between the eye-mountable device 110 and the ingestible device 120) could be determined by detecting the amount of time it takes for an in-body electrical signal to propagate between the devices. This could include emitting a first in-body electrical signal from a first device (e.g., eye-mounted device 110) and receiving the first signal using a second device (e.g., ingestible device 120). In response to receiving the first in-body electrical signal, the second device could emit a second in-body electrical signal that could be received by the first device. The first device could then determine a distance between the first and second devices or some other information about the location of the second device (e.g., an organ or section of the GI tract 105 within which the second device is located) based on a time difference between emission, by the first device, of the first in-body electrical signal and reception, by the first device, of the second in-body electrical signal. Such a determination could include reducing the time difference by a known latency between reception of an in-body electrical signal by the second device and the second device responsively emitting a further in-body electrical signal, dividing the time difference by a known and/or measured rate of propagation of in-body electrical signals in the body 101, or performing some other operations or combinations of operations.

Devices that are operable within the body 101 to communicate, using in-body electrical signals, with other devices located on or within the body 101 could be configured to facilitate a variety of applications in a variety of locations or environments within the body 101. For example, such devices could act to detect properties of the body 101, e.g., a pH, a temperature, an analyte concentration, an image, a water content, or some other information about the GI tract 105. Such devices could then transmit indications of such detected properties, via in-body electrical signals, to the eye-mountable device 110 (e.g., to be communicated to the external system 140 and/or to be presented, visually, to the eye via an LED or other display element(s) of the eye-mountable device 110) and/or to other devices within the body. In some examples, such devices could receive, via in-body electrical signals, commands to measure physiological properties of interest and could, responsive to receiving such commands, perform measurements of the physiological properties.

Additionally or alternatively, such devices could act to interact in some way with tissues or fluids of the body 101, e.g., to apply an electrical stimulus to a muscle or nerve or to deliver a drug from a reservoir of the device. Such a controlled drug release could be performed by the ingestible device 120 or by some other device that is located within the body 101 in response to receiving a command (e.g., from the 110 eye-mounted device) to release the drug or in response to detecting, using a sensor of the ingestible device 120, that a drug release should occur (e.g., to control a detected pH to be maintain the pH within a specified range of pH values). Such a drug release command could be transmitted, as an in-body electrical signal, from the eye-mounted device 110 to the ingestible device 120 (or to some other device in the body that is operable to receive in-body electrical signals) in response to the eye-mounted device 110 detecting a command gesture of a user (e.g., a specified sequence of blinks, winks, squints, eye motions, or other activities), in response to the eye-mounted device 110 detecting a physiological property of the body 101 (e.g., a glucose concentration in tears of the eye), in response to determining that the ingestible device 120 is located within a specified organ or section of the GI tract 105 (e.g., making such a determination based on a pH or other physiological property detected by the ingestible device 120, based on a distance between the eye-mountable device 110 and the ingestible device 120 that is detected using methods described elsewhere herein, and/or based on some other consideration), in response to receiving a drug release command or some other information from the external system 140, or in response to some other consideration.

In a particular example, the eye-mounted device 110 could detect a command gesture that comprises one or more blinks (e.g., by detecting an impedance between two or more electrodes of the eye-mounted device 110, by detecting an amount and/or color of light received by the eye-mounted device 110 from the environment) and, in response to detecting the command gesture, the eye-mounted device 110 could transmit an in-body electrical signal to provide a drug release command to the ingestible device 120. The ingestible device 120 could receive such a drug release command by receiving the in-body electrical signal and could responsively release an amount of a drug (e.g., insulin, an anti-nausea drug, an anti-pain drug) contained in the ingestible device 120. Thus could include operating an actuated drug reservoir that contains the drug to release a controlled amount of the drug from the drug reservoir or to release all of the drug contained in the drug reservoir. An actuated drug reservoir could include microfluidic channels, microfluidic reservoirs, electrophoretic elements (e.g., elements configured to apply generate an electrical field to control to flow or motion of a charged drug or a charged drug carrier), electrowetting elements (e.g., elements configured to wet channels of an actuated drug reservoir to control a degree of fluid contact, mass flow, and/or diffusion of a drug between a drug reservoir and tissue or fluids of the body 101), electromechanical and/or microfluidic valves, or other elements that are operable to control a timing and/or amount of drug released from the ingestible device 120 and/or from some other device that is located within a human body and that is able to transmit and/or receive in-body electrical signals.

Transmission of an in-body electrical signal can include providing square pulses, raised-cosine pulses, amplitude-modulated sinusoids, frequency- or phase-modulated sinusoids, or some other time-varying pattern of current and/or voltage via two or more electrodes that are in electrical contact with tissues and/or fluids of a body. Such time-varying patterns of current could be applied through first and second electrodes of a device (e.g., a current sourced via a first electrodes could be simultaneously sunk via a second electrode), through first and second sets of electrodes (e.g., a current sourced via a first set of electrodes that are internally electrical connected could be sunk via a second set of electrodes that are internally electrically connected), or through a plurality of electrodes according to some other configuration (e.g., time-varying currents could be sourced and/or sunk via a plurality of electrodes according to a phased array arrangement or according to some other pattern).

The timing, waveform, frequency, inter-pulse timing, or other properties of the time-varying waveforms of current and/or voltage applied, via electrodes of a device as described herein, to tissues or fluids of a body to provide in-body electrical signals could be specified to satisfy a variety of operational constraints of a device. For example, a pulse width of pulses of current provided to generate an in-body electrical signal could be sufficiently narrow (e.g., less than approximately 2 nanoseconds) to allow a distance between devices in a body (e.g., an eye-mounted device and an ingestible device) to be determined to a given resolution (e.g., at a resolution of less than approximately 1 centimeter) based on a propagation time of pulses of the in-body electrical signal between the devices. Additionally or alternatively, an inter-pulse interval between opposite-polarity pulses emitted from a device could be a sufficiently large interval (e.g., between approximately 10 nanoseconds and approximately 20 nanoseconds, for pulses that are less than approximately 5 nanoseconds wide) to prevent the opposite polarity pulses from substantially cancelling each other due to temporal spreading of the pulses as the in-body electrical signal propagates through a body.

In some examples, a pulse width, a frequency, a current or voltage amplitude, or some other properties of the electrical signals applied, via electrodes of a device, to tissues or fluids of a body to provide in-body electrical signals could be specified to prevent noxious stimulus from being provided to a recipient of the device. This could include selecting a pulse rate that is sufficiently high (e.g., higher than a few hundred Hertz) to prevent excitation of nerve fibers near the electrodes.

In further examples, a pulse width, a current or voltage amplitude, a charge balancing between negative and positive pulses, or some other properties of the electrical signals applied, via electrodes of a device, to tissues or fluids of a body to provide in-body electrical signals could be specified to prevent the electrodes of the device from being degraded and/or to prevent the electrodes of the device from generating chemical compounds that may diffuse into the body. This could include selecting pulse widths that are sufficiently narrow and/or pulse amplitudes that are sufficiently low (e.g., less than approximately 0.5 volts of pulses having widths greater than approximately 2 nanoseconds) to prevent hydrolysis or other chemical reactions from occurring at the electrodes. Additionally or alternatively, pulses of current or other time-varying currents applied to tissues or fluids of a body via a particular electrode could be charge-balanced (e.g., by following each generated pulse of current with a pulse of opposite polarity that provides a substantially equal and opposite charge to the charge provided by the preceding pulse) to prevent hydrolysis or other chemical reactions from occurring at the electrodes. Further, such electrodes could be capacitively coupled to the tissue and/or fluids and/or the electrodes could be capacitively coupled to a transmitter that generated the time-varying currents such that a mean charge sourced into and/or sunk from the body is substantially zero.

Figure 2:
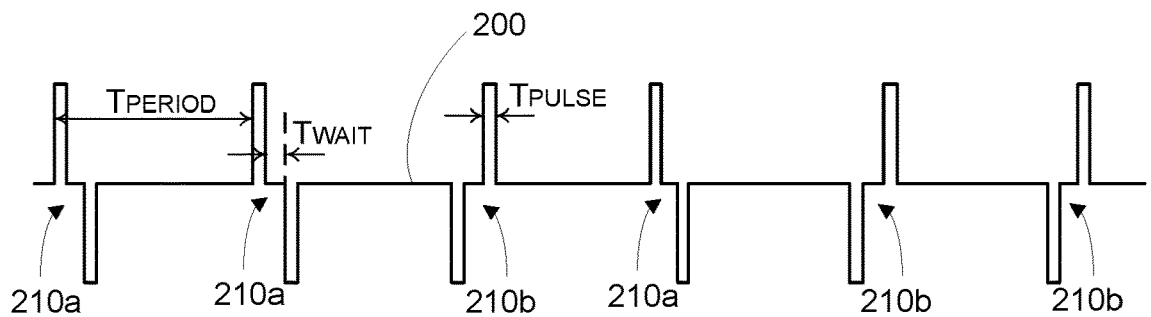
FIG. 2 illustrates an example pulse sequence of a transmitted in-body electrical signal.

FIG. 2 shows an illustrative example time-varying waveform of current 200 that could be applied, via two or more electrodes of a device, to tissues or fluids of a body to provide in-body electrical signals. The current waveform 200 includes a plurality of biphasic pulses 210a and 210b; that is, pulses of current that include a first pulse of a first polarity followed by a second pulse of opposite polarity and that delivers substantially the same magnitude of charge as the first pulse. Thus, the mean charge provided by any one of the biphasic pulses 210a, 210b is substantially zero. Such an arrangement can prevent the buildup of a steady-state potential across and/or charge on the two or more electrodes used to deliver the time-varying waveform of current 200 to tissues and/or fluids of the body.

The biphasic pulses 210a, 210b include positive-first biphasic pulses 210a (that is, biphasic pulses that include a positive-current pulse followed by a negative-current pulse) and negative-first biphasic pulses 210b (that is, biphasic pulses that include a negative-current pulse followed by a positive-current pulse). Note that the indication of positive current in FIG. 2 is a matter of arbitrarily defining the direction of positive current relative to two (or more) electrodes of a device. That is, a positive current where positive current is defined as sourcing current through a first electrode and sinking an opposite current through a second electrode can be functionally equivalent to a negative current where positive current is defined as sourcing current through the second electrode and sinking an opposite current through the first electrode.

These different types of pulse could be used to indicate information according to a variety of schemes, e.g., the positive-first biphasic pulses 210a could represent a binary '1' and the negative-first biphasic pulses 210b could represent a binary '0'. In another example, sets of biphasic pulses could represent symbols in a communication scheme (e.g., according to 8b/10b encoding), changes in the type of biphasic pulse (e.g., a biphasic pulse being the same type as a preceding biphasic pulse could represent a binary '1', while the biphasic pulse being different from the preceding biphasic pulse could represent a binary '0') could encode bits of information, or some other information relating to the polarity of the biphasic pulses, or to some other sets of pulses of a current waveform applied to tissues and/or fluids of a body via electrodes of a device, could be controlled to encode information in in-body electrical signals generated as a result of injecting such currents into a body via two or more electrodes.

As shown in FIG. 2, the biphasic pulses 210a, 210b of the time-varying current waveform 200 are equally spaced in time by a duration $T_{PERIOD}$. $T_{PERIOD}$ could be specified as being shorter and/or longer than a specified duration (e.g., shorter than approximately 10 milliseconds) such that the frequency of the biphasic pulses is greater than and/or less than a specified frequency (e.g., greater than approximately 100 Hertz) in order to prevent activation of nerve fibers by the generated in-body electrical signals or according to some other consideration. Further, note that the uniform spacing in time of the biphasic pulses in FIG. 2 is meant as a non-limiting example, and that the timing of the biphasic pulses could be controlled to encode information (e.g., according to a pulse position encoding, a pulse frequency encoding, a pulse presence encoding).

Further, the positive and negative pulses of each biphasic pulse have duration $T_{PULSE}$ and are separated in time by a duration $T_{WAIT}$. $T_{PULSE}$ could be specified as being shorter and/or longer than a specified duration according to a variety of considerations. For example, $T_{PULSE}$ could be specified to be shorter than a particular duration in order to prevent hydrolysis or other chemical reactions from occurring on an electrode. Such a particular duration could be specified relative to an amplitude of the pulses, e.g., a lower-amplitude pulse could have a longer duration without causing hydrolysis or other chemical reactions. In another example, $T_{PULSE}$ could be specified to be shorter than a specified duration (e.g., shorter than approximately 2 nanoseconds) such that the timing of a pulse of an in-body electrical signal could be detected, at a distance by another device within a body, to determine a distance between the generating device and the receiving device to a desired level of accuracy (e.g., less than approximately 1 centimeter). Further, the separation $T_{WAIT}$ could be made such that the negative and positive pulses of each biphasic pulse do not cancel out due to spreading of the pulses associated with propagation of in-body electrical signals over an expected distance of propagation (e.g., $T_{WAIT}$ could be between approximately 10 nanoseconds and approximately 20 nanoseconds). Such specifications could be made relative to an expected distance or range of distances between first and second devices and/or to an expected degree of pulse spreading associated with propagation of in-body electrical signals over such an expected distance. Note that the uniform width of the pulses ($T_{PULSE}$) and inter-pulse durations ($T_{WAIT}$) in FIG. 2 are meant as a non-limiting example, and that the widths and/or timings of pulses of voltage and/or current used to generate in-body electrical signals could be controlled to encode information (e.g., according to a pulse width encoding) or according to some other consideration.

III. Example Eye-Mountable Devices

As noted above, a body-mountable device can, when mounted to an external body surface such that electrodes of the device are in contact with fluid of a body, provide access to in-body electrical signals from devices located within the body and/or can act to generate such in-body electrical signals that could be received by such devices. Contact with tear fluid of the eye (e.g., tear fluid disposed between the eye-mountable device and the cornea of the eye, between the eye-mountable device and an eyelid of the eye, or disposed in some other location of the eye), or with some other fluid of the body (e.g., saliva, subcutaneous or cutaneous interstitial fluid) can provide a low-impedance electrical connection between a plurality of electrodes (e.g., two or more electrodes) of the body-mountable device and tissue and/or fluids of the body through which such in-body electrical signals can propagate. Further, location of the body-mountable device on the surface of the body (i.e., on the surface of an eye) can facilitate transmission and/or reception of wireless signals (e.g., optical signals, radio frequency signals) by the body-mountable device such that the body-mountable device can communicate with and/or be powered by external devices (e.g., a cellphone, a tablet, a computer, a server, a wearable device, an insulin pump or other medical device).

Such a body-mountable device could be an eye-mountable device configured to be removably mounted to a corneal surface of the eye (e.g., could be formed as a rigid or soft contact lens), to be mounted beneath an eyelid of the eye (e.g., to be placed between the lower eyelid and the cornea), or to be removably mounted to some other location of an eye such that two or more electrodes of the device are in at least intermittent electrical contact with tissues and/or fluids of the body (e.g., in electrical contact with tear fluid of the eye such that in-body electrical signals can be transmitted from and/or received by the electrodes of the device). Further, by being removably mounted to an external surface of the body, such an eye-mountable device can be removed from the eye to be recharged, to transfer data with an external system (e.g., to upload recorded images or other physiological data received, via in-body electrical signals, from an ingestible device), or to perform some other functions.

Figure 3A:
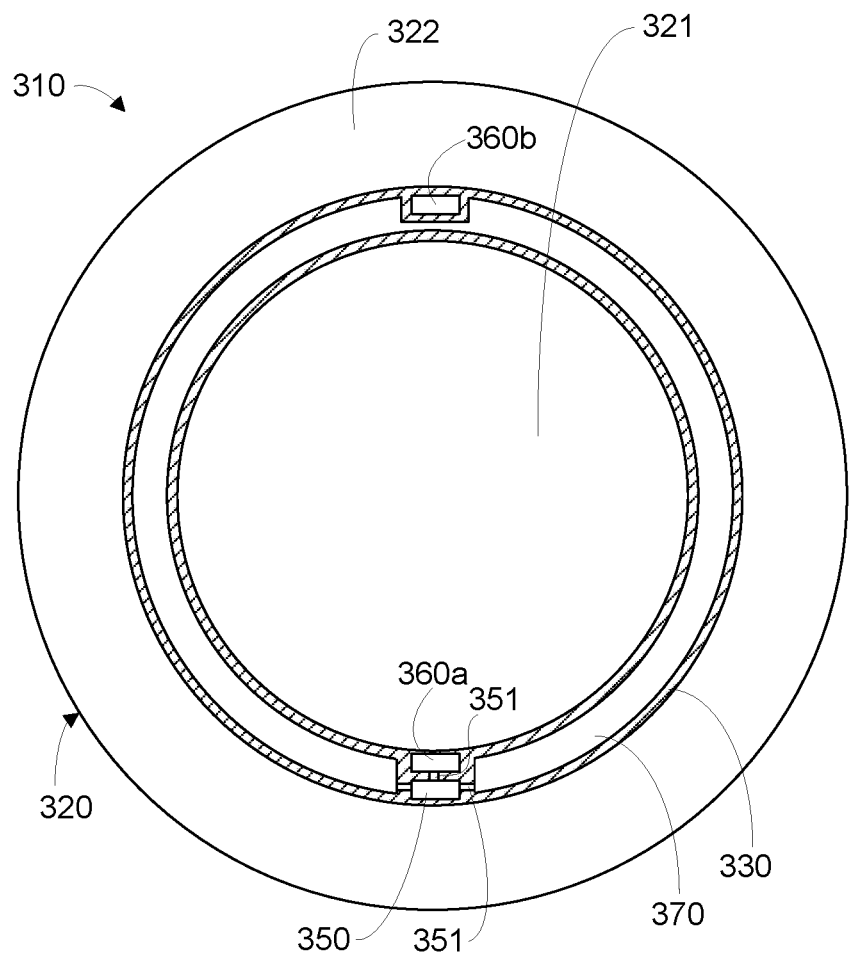
FIG. 3A is a top view of an example eye-mountable device.
Figure 3B:
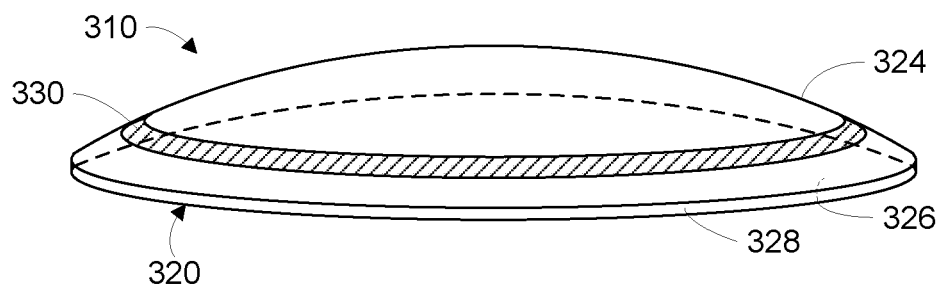
FIG. 3B is an aspect view of the example eye-mountable device shown in FIG. 3A.

FIG. 3A is a top view of an example eye-mountable device 310. FIG. 3B is an aspect view of the example eye-mountable device shown in FIG. 3A. It is noted that relative dimensions in FIGS. 3A and 3B are not necessarily to scale, but have been rendered for purposes of explanation only in describing the arrangement of the example eye-mountable device 310. The eye-mountable device 310 is formed of a polymeric material 320 shaped as a curved disk. The polymeric material 320 can be a substantially transparent material to allow incident light to be transmitted to the eye while the eye-mountable device 310 is mounted to the eye. The polymeric material 320 can be a biocompatible material similar to those employed to form vision correction and/or cosmetic contact lenses in optometry, such as polyethylene terephthalate ("PET"), polymethyl methacrylate ("PMMA"), silicone hydrogels, combinations of these, etc. The polymeric material 320 can be formed with one side having a concave surface 326 suitable to fit over a corneal surface of an eye. The opposing side of the disk can have a convex surface 324 that does not interfere with eyelid motion while the eye-mountable device 310 is mounted to the eye. A circular outer side edge 328 connects the concave surface 324 and convex surface 326.

The eye-mountable device 310 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 310 can be selected according to the size and/or shape of the corneal surface of the wearer's eye.

The polymeric material 320 can be formed with a curved shape in a variety of ways. For example, techniques similar to those employed to form vision-correction contact lenses, such as heat molding, injection molding, spin casting, etc. can be employed to form the polymeric material 320. While the eye-mountable device 310 is mounted in an eye, the convex surface 324 faces outward to the ambient environment while the concave surface 326 faces inward, toward the corneal surface. The convex surface 324 can therefore be considered an outer, top surface of the eye-mountable device 110 whereas the concave surface 326 can be considered an inner, bottom surface. The "top" view shown in FIG. 3A is facing the convex surface 324. From the top view shown in FIG. 3A, the outer periphery 322, near the outer circumference of the curved disk is curved into the page, whereas the center region 321, near the center of the disk is curved out of the page.

A substrate 330 is embedded in the polymeric material 320. The substrate 330 can be embedded to be situated along the outer periphery 322 of the polymeric material 320, away from the center region 321. The substrate 330 does not interfere with vision because it is too close to the eye to be in focus and is positioned away from the center region 321 where incident light is transmitted to the eye-sensing portions of the eye. Moreover, the substrate 330 can be formed of a transparent material to further mitigate any effects on visual perception.

The substrate 330 can be shaped as a flat, circular ring (e.g., a disk with a central hole). The flat surface of the substrate 330 (e.g., along the radial width) is a platform for mounting electronics such as chips (e.g., via flip-chip mounting) and for patterning conductive materials (e.g., via deposition techniques) to form electrodes (e.g., a plurality of electrodes operable to transmit and/or receive in-body electrical signals, an anode and/or cathode of an electrochemical battery, electrodes of an electrochemical sensor), antenna(e), and/or connections. The substrate 330 and the polymeric material 320 can be approximately cylindrically symmetric about a common central axis. The substrate 330 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 330 can be implemented in a variety of different form factors.

A loop antenna 370, controller 350, and first 360*a* and second 360*b* electrodes are disposed on the embedded substrate 330. The controller 350 can be a chip including logic elements configured to transmit and/or receive, using the electrodes 360*a*, 360*b*, in-body electrical signals and to operate the loop antenna 370. The controller 350 is electrically connected to the loop antenna 370, electrodes 360*a*, 360*b*, and any other electronic elements of the eye mountable device 310 by interconnects 351 also situated on the substrate 330. The interconnects 351, the loop antenna 370, the electrodes 360*a*, 360*b*, and any other conductive electrodes (e.g., an anode and cathode of an electrochemical battery, for an electrochemical ion sensor, etc.) can be formed from conductive materials patterned on the substrate 330 by a process for precisely patterning such materials, such as deposition, lithography, etc. The conductive materials patterned on the substrate 330 can be, for example, gold, platinum, palladium, titanium, carbon, aluminum, copper, silver, silver-chloride, conductors formed from noble materials, metals, combinations of these, etc.

As shown in FIG. 3A, which is a view facing the convex surface 324 of the eye-mountable device 310, the first 360*a* and second 360*b* electrodes are mounted to a side of the substrate 330 facing the convex surface 324. However, the electronics, electrodes 360*a*, 360*b*, etc. situated on the substrate 330 can be mounted to either the "inward" facing side (e.g., situated closest to the concave surface 326) or the "outward" facing side (e.g., situated closest to the convex surface 324). Moreover, in some embodiments, some electronic components can be mounted on one side of the substrate 330, while other electronic components are mounted to the opposing side, and connections between the two can be made via conductive materials passing through the substrate 330.

The loop antenna 370 can be a layer of conductive material patterned along the flat surface of the substrate to form a flat conductive ring. In some instances, the loop antenna 370 can be formed without making a complete loop. For instance, the antenna 370 can have a cutout to allow room for the controller 350 and electrodes 360*a*, 360*b*, as illustrated in FIG. 3A. However, the loop antenna 370 can also be arranged as a continuous strip of conductive material that wraps entirely around the flat surface of the substrate 330 one or more times. For example, a strip of conductive material with multiple windings can be patterned on the side of the substrate 330 opposite the controller 350 and electrodes 360*a*, 360*b*. Interconnects between the ends of such a wound antenna (e.g., the antenna leads) can be passed through the substrate 330 to the controller 350.

Figure 3D:
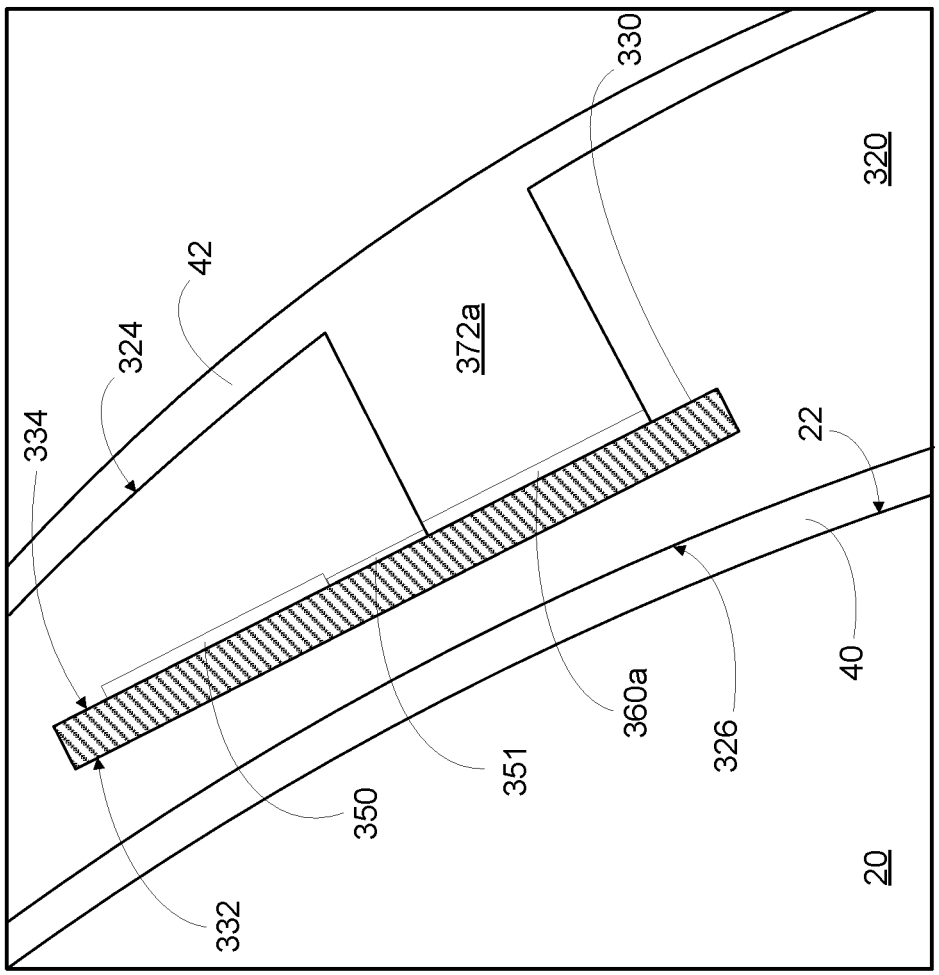
FIG. 3D is a side cross-section view enhanced to show the tear film layers surrounding the surfaces of the example eye-mountable device when mounted as shown in FIG. 3C.
Figure 3C:
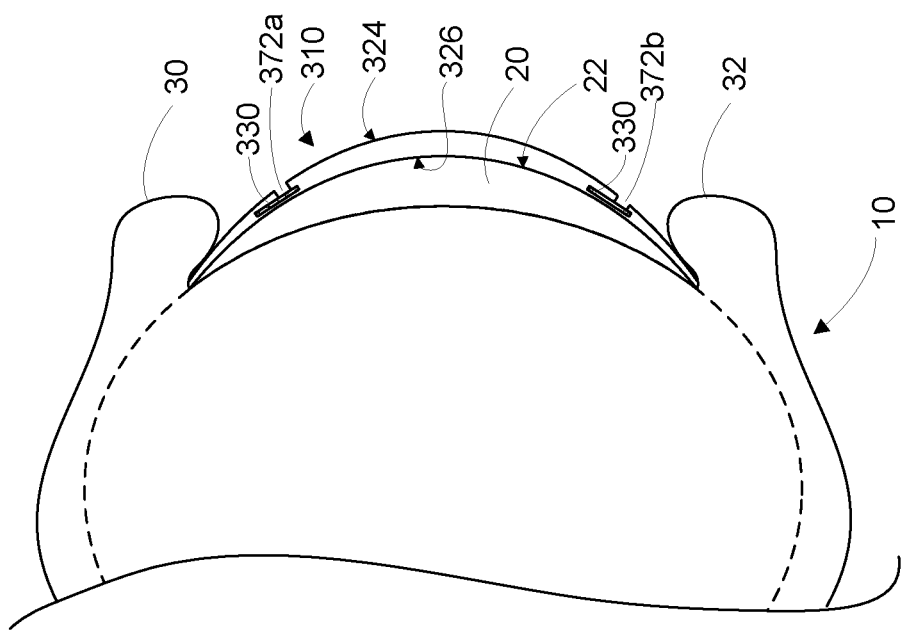
FIG. 3C is a side cross-section view of the example eye-mountable device shown in FIGS. 3A and 3B while mounted to a corneal surface of an eye.

FIG. 3C is a side cross-section view of the example eye-mountable device 310 while mounted to a corneal surface 22 of an eye 10. FIG. 3D is a close-in side cross-section view enhanced to show the tear film layers 40, 42 surrounding the exposed surfaces 324, 326 of the example eye-mountable device 310. It is noted that relative dimensions in FIGS. 3C and 3D are not necessarily to scale, but have been rendered for purposes of explanation only in describing the arrangement of the example eye-mountable device 310. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous fluid secreted by the lacrimal gland to protect and lubricate the eye 10. When the eye-mountable device 110 is mounted in the eye 10, the tear film coats both the concave and convex surfaces 124, 126 with an inner layer 40 (along the concave surface 126) and an outer layer 42 (along the convex layer 124). The tear film layers 40, 42 can be about 10 micrometers in thickness and together account for about 10 microliters. The tear film layer 40 on the corneal surface 22 also facilitates mounting the eye-mountable device 310 by capillary forces between the concave surface 326 and the corneal surface 22. In some embodiments, the eye-mountable device 310 can also be held over the eye in part by vacuum forces against corneal surface 22 due to the concave curvature of the eye-facing concave surface 326.

As shown in the cross-sectional views in FIGS. 3C and 3D, the substrate 330 can be inclined such that the flat mounting surfaces of the substrate 330 are approximately parallel to the adjacent portion of the concave surface 326. As described above, the substrate 330 is a flattened ring with an inward-facing surface 332 (closer to the concave surface 326 of the polymeric material 320) and an outward-facing surface 334 (closer to the convex surface 324). The substrate 330 can have electronic components and/or patterned conductive materials mounted to either or both mounting surfaces 332, 334. As shown in FIG. 3D, the electrodes 360*a*, 360*b*, controller 350, and conductive interconnects 351 are mounted on the outward-facing surface 334 such that the electrodes 360*a*, 360*b* are relatively closer in proximity to the outer tear film layer 42 than if it was mounted on the inward-facing surface 332. With this arrangement, the electrodes 360*a*, 360*b* can be operated to transmit and/or receive in-body electrical signals when one or both of the eyelids 30, 32 are closed such that the electrodes 360*a*, 360*b* have a relatively low-impedance electrical contact with tissues and/or fluids of the body via the outer tear film 42 and the tissues of the eyelid(s) 30, 32.

In such an outward-facing configuration, the electrodes 360*a*, 360*b*, could also be used to detect whether the eyelid(s) are closed over the electrodes 360*a*, 360*b* (or over some additionally outward-facing electrodes of a further plurality of electrodes of the device 310). Such detection could allow the detection of blinks, winks, or other command gestures of the eye. Additionally or alternatively, such detection could provide information for the timing of transmission and/or reception of in-body electrical signals via a plurality of outward-facing electrodes (e.g., 360*a*, 360*b*). That is, the controller 350 could operate to transmit and/or receive, via the outward-facing electrodes (e.g., 360*a*, 360*b*), in-body electrical signals when it has been detected, using the outward-facing electrodes, that a plurality of the outward-facing electrodes are in electrical contact with the eyelid(s) 30, 32. However, in other examples, the device 310 may additionally or alternatively include a plurality of electrodes disposed on the inward-facing surface 332 of the substrate 330 such that a plurality of electrodes of the device 310 are facing the convex surface 324 and able to substantially continuously transmit and/or receive in-body electrical signals via the inner tear film layer 40.

Note that the electrodes 360a, 360b being exposed directly to the environment of the eye-mountable device 310 (e.g., exposed directly to fluids received from the outer tear layer 42 via the channel 372) is meant as a non-limiting example. For example, electrodes used to transmit and/or receive in-body electrical signals could include a protective coating that is disposed over the electrodes and that is permeable to water and ions from an aqueous fluid, e.g., from the tear fluid and/or from a storage medium in which the eye-mountable device 310 is stored before and/or after mounting to the eye 10. Such a protective coating could be a hydrogel or other material that is permeable to water and ions and that has a hardness, a stiffness, a resilience, or some other property specified to protect the electrodes. For example, the protective coating could be a hydrogel that includes units of hydroxyethyl methacrylate. The protective coating could include one or more polymers, including polydimethylsiloxane, polyvinylchloride, polyethylene terephthalate, polymethyl methacrylate, silicone hydrogels, or combinations of these or other polymers. The embodiments herein are meant only as illustrative examples; other protective coatings and electrode materials are anticipated.

Note that the illustrated eye-mountable device 310 having two electrodes 360a, 360b disposed on opposite sides of that device 310 and facing an outer surface of the device 310 is intended as a non-limiting example of an eye-mountable device that is operable to transmit and/or receive in-body electrical signals using a plurality of electrodes of the eye-mountable device. Generally, such electrodes will be disposed on an eye-mountable device such that distances between pairs of the electrodes are maximized (e.g., such that pairs of electrodes are disposed proximate to opposite edges of the eye-mountable device). Disposition of electrodes to maximize the inter-electrode distance in this way can increase the distance at which in-body electrical signals can be detected when the electrodes are used to transmit the in-body electrical signals (e.g., by increasing a dipole moment of the electrical field generated by the application of currents or voltages to the electrodes). Further, by increasing a distance between a pair of electrodes used to detect an in-body electrical signal, in-body electrical signals transmitted from devices that are distant from the eye-mountable device, within the body, can be detected (e.g., due to an increased magnitude of voltages detected using the pair of electrodes related to sampling of the biopotential within the body across an increased distance). Electrodes of the eye-mountable device 310 could also be used to communicate with an external device and/or to receive power (e.g., to recharge a battery of the eye-mountable device) when electrodes of the eye-mountable device 310 are placed in electrical contact with electrodes of the external device (e.g., via direct contact between electrodes of the devices and/or via electrical contact through saline or some other conductive fluid).

Eye-mountable devices that include more than two electrodes could select pairs of electrodes through which to transmit and/or receive in-body electrical signals, e.g., to improve reception of generated signals by another device and/or to improve reception of signals from another device. This could include selecting a pair of electrodes of a plurality of electrodes of the device such that an intensity of in-body signals, detected as a voltage or other electrical signals by another device, is increased relative to other possible pairs of electrodes of the eye-mountable device. Such selection could include using a variety of different pairs of electrodes to transmit in-body electrical signals to another device and receiving from the other device (e.g., via further in-body electrical signals transmitted from the other device) a magnitude of the in-body electrical signal detected by the other device in response to use of each of the different pairs of electrodes to transmit in-body electrical signals.

The loop antenna 370 is intended as a non-limiting example of means for transmitting and/or receiving radio frequency signals (or other wireless electromagnetic signals) and/or radio frequency wireless power from an external device. Such radio frequency signals could be used to transmit information from the eye-mountable device 310 to an external system (e.g., images or other physiological data received by the eye-mountable device 310, via in-body electrical signals, from an ingestible device or some other device located within a body) and/or to receive information from an external system (e.g., drug release commands from an external controller or user interface that could then be transmitted, via in-body electrical signals, to an ingestible device that is located within a body and that includes means for controlling the release of a drug from a drug reservoir of the ingestible device). An eye-mountable device could additionally or alternatively include a patch antenna, a fractal antenna, a dipole antenna, or some other means for transmitting and/or receiving radio frequency signals to and/or from an external device.

Note that an eye-mountable device as described herein (e.g., 310) could include additional or alternative means for wireless communication and/or wireless power reception. For example, an eye-mountable device could include light emitters (e.g., infrared, visible, and/or ultraviolet LEDs or lasers) and/or light detectors (e.g., photodiodes, phototransistors) that are configured to transmit and/or receive optical signals from an external system in order to communicate, via the optical signals, with the external system.

Further, an eye-mountable device as described herein (e.g., 310) could include a user interface or other means for indicating information to a wearer and/or for receiving commands from the wearer. This could include providing, to the wearer, an indication of information about a property of the wearer's body that has been detected by a device within the wearer's body (e.g., by a 'smart pill' or other ingestible device) and transmitted, via in-body electrical signals, from the device within the wearer's body to the eye-mountable device. Such a user interface could be operable to provide an optical indication (e.g., to emit light toward the eye of the wearer), a mechanical indication (e.g., a mechanical or acoustical vibration), or some other indication that may be perceived by a wearer such that the wearer becomes aware of some information indicated by the eye-mountable device (e.g., that a detected physiological parameter is outside of some specified range, that a detected physiological parameter is such that the wearer should take a drug or engage in some other treatment). Such a user interface could include one or more LEDs, displays, or other elements configured to provide an optical indication to the wearer by emitted patterns of light toward the retina of the eye of the wearer (e.g., by emitting a pattern of light indicative of a detected physiological property or other information).

The eye-mountable devices described herein (e.g., 310) could include one or more sensors (not shown) configured to detect physiological parameters of a body (e.g., concentrations of analytes in tears or other bodily fluids, whether an eyelid is closed), properties of the environment of the device (e.g., an ambient illumination, a barometric pressure, a temperature), properties of the device (e.g., an acceleration, an orientation), or to detect some other information. Such sensors could include accelerometers, electrodes (e.g., electrodes of electrochemical analyte sensors, an electrooculogram, or some other bioelectrical signal), light detectors, thermometers, gyroscopes, capacitance sensors, pressure sensors, strain gauges, light emitters, microphones, or other elements configured to detect one or more physical variables related to a property of interest. The eye-mountable devices as shown here could operate such elements to measure physiological parameters or other information of interest at one or more points in time. Such measured properties and/or parameters could be recorded (e.g., in a memory of the device, for example, for later transmission to an external system), transmitted to an external system, indicated using elements of the device (e.g., using a display, using one or more light-emitting elements), used to determine a health state of a user, or used according to some other application. Additionally or alternatively, the eye-mountable device could operate such elements (e.g., LEDs, displays, antennas, optical data transmitters) to provide indications of physiological parameters or other information received, via in-body electrical signals, from devices disposed within a body to which the eye-mountable device is mounted.

IV. Example Ingestible Devices

As noted above, a variety of devices could be disposed within a human body (e.g., via implantation, injection, catherization, ingestion) and operable within the human body to transmit and/or receive in-body electrical signals. Such devices could include a plurality of electrodes (e.g., two or more electrodes for each device) configured to provide electrical contact with tissues and/or fluids of the body such that the in-body electrical signals can be transmitted and/or received via the plurality of electrodes of each device. Such devices could be configured to detect physiological properties of the body (e.g., a pH, an image of a tissue or cavity of the body, a concentration of an analyte, a biopotential related to electrical activity of the heart, a nerve, a muscle, and/or some other electrically active tissue). Additionally or alternatively, such devices could be configured to interact with tissues and/or fluids of the body in some other way. This could include providing, via electrodes of the device (e.g., the same electrodes used to transmit and/or receive in-body electrical signals), electrical stimulation to tissues of the body (e.g., to control the beating of a heart, to provide a sensory perception via stimulation of a sensory nerve, to cause contraction of a muscle via stimulation of a motor nerve). Additionally or alternatively, such a device could provide, in a controlled fashion, a drug (e.g., an analgesic, an anti-nausea drug) or some other chemical substance (e.g., an antacid, a probiotic, a digestive enzyme) to tissues or fluids of the body.

A device as described herein providing a drug could include operating an actuated drug reservoir of the device to deliver all of the drug in the actuated drug reservoir and/or to provide a controlled amount of drug from the drug reservoir. Such a drug delivery could be performed in response to detecting a property of the body (e.g., detecting that a pH of fluids proximate the device is within a range of pH values characteristic of a particular organ or section of a GI tract), in response to detecting the location of the device (e.g., detecting a distance between the device and an body-mountable device based on a propagation time of in-body electrical signals between the device and the body-mountable device), or in response to receiving, via in-body electrical signals, a drug release command (e.g., a drug release command transmitted from a body-mountable device in response to the body-mountable device detecting a command gesture, receiving a drug release command or some other information from an external system, or in response to some other consideration).

As noted above, a device that is operable within a human body to receive and/or transmit in-body electrical signals could be operable within a GI tract of the body. Such a device could be an ingestible device, e.g., a device that has a size and/or shape specified such that a person could swallow the ingestible device and further such that the ingestible device can be transported through the GI tract by the operation of the GI tract (e.g., by peristalsis through the intestines). Such an ingestible device could include a coating or other sealant means to prevent fluids in the gastrointestinal environment from entering the device and/or damaging the components of the device. Such an ingestible device, which includes electronics, may be referred to as a 'smart pill'.

Figure 4:
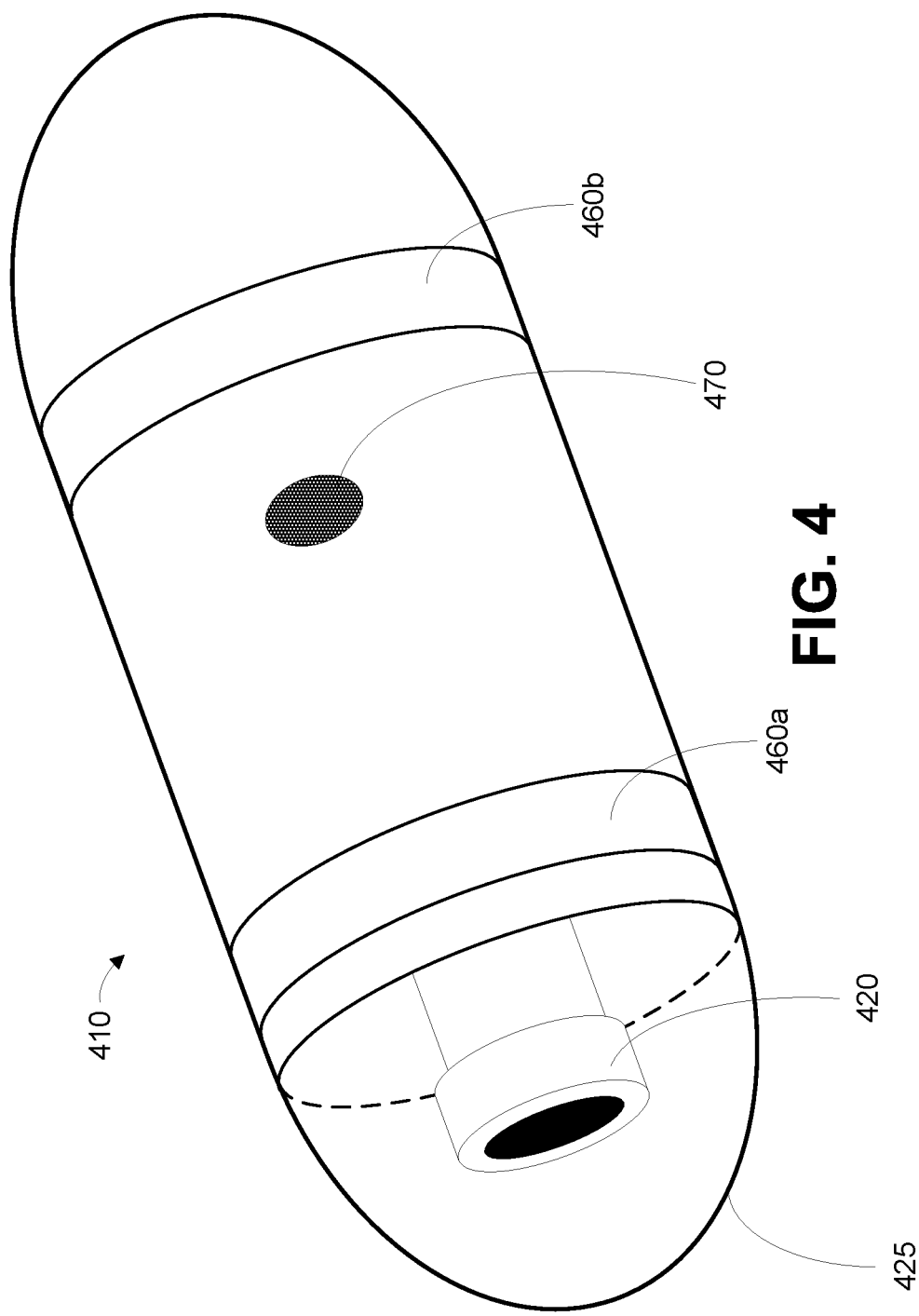
FIG. 4 is a perspective view of an example ingestible device.

FIG. 4 shows an example ingestible device 410. The device has a rounded cylindrical shape in order to, e.g., facilitate swallowing of the device and/or transport of the device through the GI tract by the actions of organs of the GI tract (e.g., via peristalsis, via viscous fluid flows). One of the rounded ends of the ingestible device 410 is formed of a transparent window 425 such that a camera 420 within the device can generate images of the inside of the GI tract and/or of contents of the GI tract. The ingestible device 410 also includes a port 470 through which drugs or other substances may be emitted from a reservoir of the ingestible device 410 into the body. The ingestible device 410 also includes first 460a and second 460b electrodes configured to provide electrical contact with tissues and/or fluids of the GI tract, e.g., to facilitate transmission and/or reception of in-body electrical signals, to detect biopotentials, to provide electrical stimulus, or to provide some other functionality. The ingestible device 410 may include additional elements, e.g., a battery, a controller, a memory, a transmitter and/or receiver, or some other elements configured to provide some functionality of the ingestible device 140.

As shown in FIG. 4, the ingestible device 410 includes two ring-shaped electrodes 460a, 460b located at opposite ends of the device 410. Location of the electrodes at opposite end of the device 410, or otherwise increasing the distance between one or more pairs of electrodes of the device 410, can increase the distance at which in-body electrical signals can be detected when the electrodes 460a, 460b are used to transmit the in-body electrical signals (e.g., by increasing a dipole moment of the electrical field generated by the application of currents or voltages to the electrodes). Further, by increasing a distance between a pair of electrodes used to detect an in-body electrical signal, in-body electrical signals transmitted from devices that are distant from the ingestible device, on or within the body, can be detected (e.g., due to an increased magnitude of voltages detected using the pair of electrodes related to sampling of the biopotential within the body across an increased distance).

Note that the illustrated two ring-shaped electrodes are intended as a non-limiting embodiment of electrodes of an ingestible device (or of a device that is otherwise operable within a body to transmit and/or receive in-body electrical signals). A device (e.g., the ingestible device 410) could include additional electrodes, e.g., a plurality of ring-shaped, circular, or otherwise configured electrodes disposed on an outer surface of the device. In some examples, this could include disposing one or more electrodes at the end of an insulated lead or other extended structure in order to increase a distance between one or more pairs of electrodes. Such an insulated lead could be flexible, e.g., to facilitate transport of an ingestible device through a GI tract. Further, in examples wherein the insulated lead is part of an ingestible device, the insulated lead could be initially adhered against the side of the ingestible device to facilitate swallowing of the device. Following ingestion of the device, the insulated lead could extend away from the ingestible device, e.g., due to dissolution, by gastrointestinal fluids, of an adhesive material that adhered the insulated lead to the side of the ingestible device before being swallowed. Other configurations of electrodes of an ingestible device, or of some other device that is operable within a body to send and/or receive in-body electrical signals within the body, are anticipated.

As noted above, an ingestible device could include an actuated drug reservoir that could be operated to provide, in a controlled fashion, a drug or other substance into a body. Thus could include operating the actuated drug reservoir to release a controlled amount of the drug from the drug reservoir or to release all of the drug contained in the drug reservoir. An actuated drug reservoir could include microfluidic channels, microfluidic reservoirs, electrophoretic elements (e.g., elements configured to apply generate an electrical field to control to flow or motion of a charged drug or a charged drug carrier), electrowetting elements (e.g., elements configured to wet channels of an actuated drug reservoir to control a degree of fluid contact, mass flow, and/or diffusion of a drug between a drug reservoir and tissue or fluids of a body), electromechanical and/or microfluidic valves, or other elements that are operable to control a timing and/or amount of drug released from the ingestible device 410 and/or from some other device that is located within a human body and that is able to transmit and/or receive in-body electrical signals. In some examples, the ingestible device 410 could include multiple actuated drug reservoirs that are independently operable to release all of the drug contained in each drug reservoir. In such an example, releasing a controlled amount of a drug into a body from such an ingestible device could include operated a specified number of the multiple drug reservoirs to release the drug into the body.

The ingestible devices (e.g., 410) or otherwise-configured devices operable within a human body to transmit and/or receive in-body electrical signals described herein could include one or more sensors configured to detect physiological parameters of a body (e.g., concentrations of analytes in chyme or other bodily fluids, pressure or forces within a lumen or other volume of a GI tract, biopotentials), properties of the environment of the device (e.g., a temperature), properties of the device (e.g., an acceleration, an orientation), or to detect some other information. Such sensors could include accelerometers, electrodes (e.g., electrodes of electrochemical analyte sensors, an electromyogram, an electrocardiogram, or some other bioelectrical signal), light detectors, thermometers, gyroscopes, capacitance sensors, pressure sensors, strain gauges, light emitters, microphones, or other elements configured to detect one or more physical variables related to a property of interest. The ingestible devices as shown here could operate such elements to measure physiological parameters or other information of interest at one or more points in time. Such measured properties and/or parameters could be recorded (e.g., in a memory of the device, for example, for later transmission, via in-body electrical signals to a body-mounted device), transmitted to a body-mounted device, used to determine a health state of a user, or used according to some other application.

V. Example Electronics of a Body-Mountable Device

Figure 5:
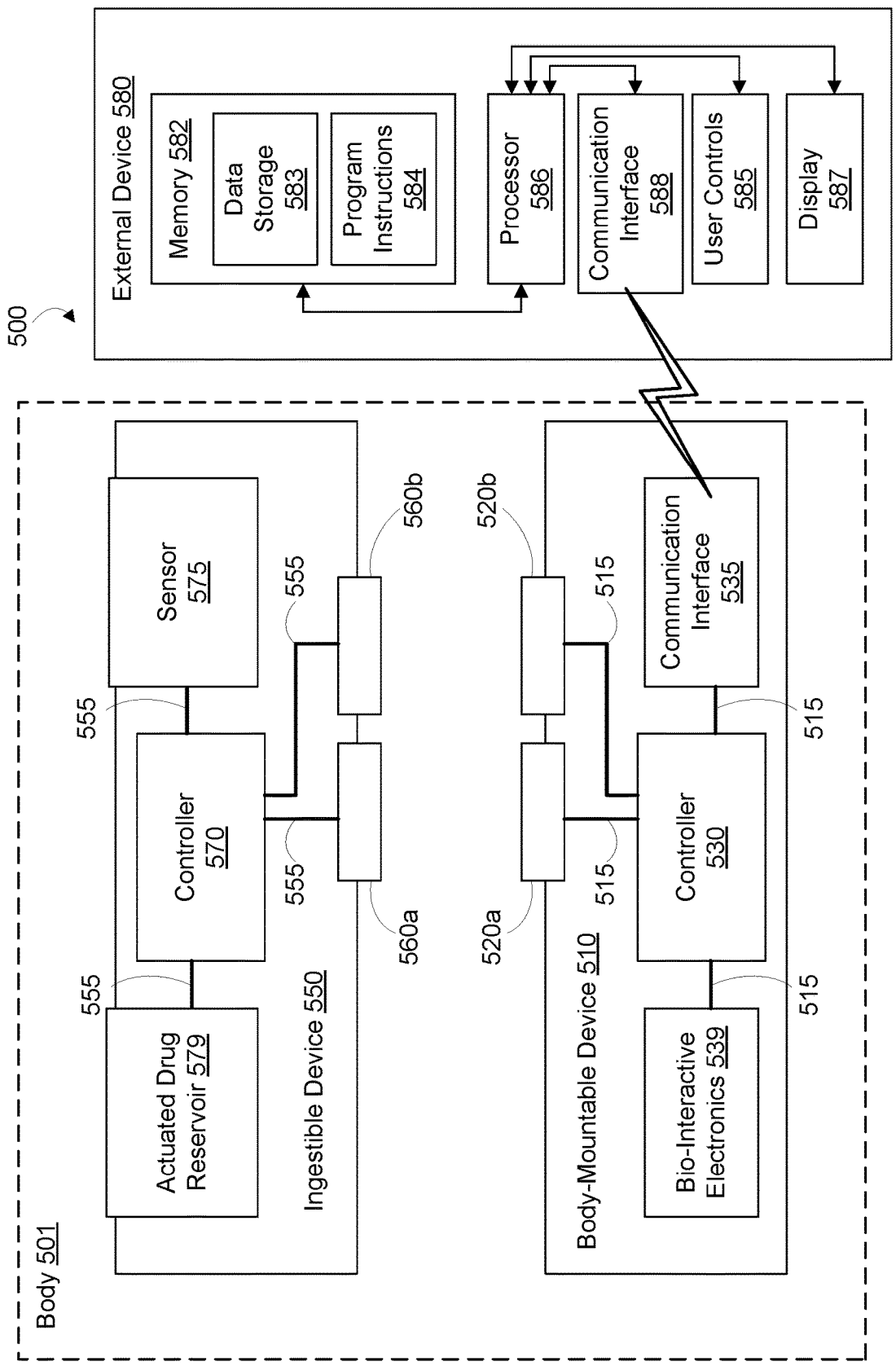
FIG. 5 is a block diagram of an example system that includes an eye-mountable device in wireless communication with an external reader and in communication with an ingestible device via transmission of in-body electrical signals.

FIG. 5 is a block diagram of a system 500 that includes a body-mountable device 510 in communication, via in-body electrical signals, with an ingestible device 550. The body-mountable device 510 is also in wireless communication with an external device 580. As shown indicated by dashed lines in FIG. 5, the ingestible device 550 and body-mountable device 510 are disposed on or within a body such that electrodes of the devices 510, 550 are in electrical contact with tissues and/or fluids of the body 501 such that in-body electrical signal can be transmitted from one of the devices to the other via propagation of the in-body electrical signals through the body 501. The ingestible device is located within a body 501 (e.g., within a GI tract of the body) and the body-mountable device 510 is located on an external surface of the body (e.g., on an eye of the body). Exposed regions of the body-mountable device 510 may be made of a polymeric material or other material(s) formed to be contact-mounted to a body surface, e.g. to a corneal surface of the eye. Additionally or alternatively, the body-mountable device 510 may be configured to be mounted to an external body surface using an adhesive, e.g., to a skin surface such that electrodes of the device 510 penetrate the skin to access interstitial fluid beneath or within the skin.

The body-mountable device 510 includes a controller 530, bio-interactive electronics 539, first 520*a* and second 520*b* electrodes that provide an electrical connection to tissues and/or fluids of the body 501, and a communication interface 535. The bio-interactive electronics 539 are configured to detect physiological properties (e.g., a glucose concentration in tears), to detect command gestures (e.g., movements of an eye and/or eyelids), to provide indications to a user (e.g., by emitting light from an LED and/or display), or to otherwise interact with the body 501 and are operated by the controller 530. The electrodes 520*a*, 520*b* can be operated to receive (e.g., by detecting time-varying patterns of voltage across the electrodes 520*a*, 520*b*) and/or transmit (e.g., by applying time-varying patterns of voltage across and/or current through the electrodes 520*a*, 520*b*) in-body electrical signals, e.g., to communicate with the ingestible device 550. The communication interface 535 includes one or more antennas, light emitter, light receivers, amplifiers, oscillators, mixers, modulators, or other elements that can be operated by the controller 530 to wirelessly communicate information between the body-mountable device 510 and the external device 580 via radio frequency signals, optical signals, or some other wireless signals. The communication interface 535, the controller 530, the electrodes 520*a*, 520*b*, and the bio-interactive electronics 539 can all be connected together via interconnects 515, e.g., via patterns metallic traces formed on a substrate material on which the components (e.g., 535, 530, 539) are disposed. Further, the electrodes 520*a*, 520*b* could comprise metallic traces or patterns formed on such a substrate material.

To facilitate contact-mounting to an eye, a polymeric material of the body-mountable device 510 can have a concave surface configured to adhere ("mount") to a moistened corneal surface (e.g., by capillary forces with a tear film coating the corneal surface). Additionally or alternatively, the body-mountable device 510 can be adhered by a vacuum force between the corneal surface and the polymeric material due to the concave curvature. While mounted with the concave surface against the eye, the outward-facing surface of the polymeric material can have a convex curvature that is formed to not interfere with eye-lid motion while the body-mountable device 510 is mounted to the eye. For example, the polymeric material can be a substantially transparent curved polymeric disk shaped similarly to a contact lens.

In examples wherein the body-mountable device 510 is such an eye-mountable device, the electrodes 520a, 520b could be disposed on the concave surface against the eye to provide an electrical connection, via the tear fluid and cornea of the eye, to tissue and/or fluids of the body such that in-body electrical signals can be transmitted between the body-mountable device 510 and the ingestible device 550 when the body-mountable device 510 is mounted to an eye and the ingestible device 550 is located in a GI tract. Alternatively, the electrodes 520a, 520b could be disposed on the convex surface against the eye to provide an electrical connection, via the tear fluid and eyelid(s) of the eye, to tissue and/or fluids of the body such that in-body electrical signals can be transmitted between the body-mountable device 510 and the ingestible device 550 when the body-mountable device 510 is mounted to an eye, the ingestible device 550 is located in a GI tract, and the eyelid(s) are covering the electrodes. Note that the body-mountable device could include further electrodes (e.g., a plurality of electrodes located on one or both sides of the body-mountable device 510, e.g., at a plurality of locations around the periphery of the body-mountable device 510).

The body-mountable device 510 could be powered in a variety of ways. For example, the body-mountable device 510 could include an electrochemical battery and/or ultracapacitor to store energy for use by the device 510. Additionally or alternatively, the device 510 could include means for harvesting wireless energy (e.g., radio frequency energy, optical energy). For example, a radio-frequency energy-harvesting antenna (e.g., an antenna of the communication interface 535) can capture energy from incident radio radiation. In another example, a photovoltaic cell or other optical energy receiving element(s) could receive energy from the ambient illumination present in the environment of the device 510 and/or optical energy emitted from an external device (e.g., from the external device 580).

The ingestible device 550 includes a controller 570, a sensor 575, first 560a and second 560b electrodes that provide an electrical connection to tissues and/or fluids of the body 501, and an actuated drug reservoir 579. The sensor 575 is configured to detect a physiological property of the body (e.g., a pH or an analyte concentration in fluids of the GI tract, an image of tissues and/or contents of the GI tract, a biopotential within the GI tract, a pressure within the GI tract) and is operated by the controller 570. The electrodes 560a, 560b can be operated to receive (e.g., by detecting time-varying patterns of voltage across the electrodes 560a, 560b) and/or transmit (e.g., by applying time-varying patterns of voltage across and/or current through the electrodes 560a, 560b) in-body electrical signals, e.g., to communicate with the body-mountable device 510. The actuated drug reservoir 579 includes a reservoir of a drug or other substance and can be operated to release a controlled amount of the drug from the reservoir or to release all of the drug contained in the reservoir. The actuated drug reservoir 579, the controller 570, the electrodes 560a, 560b, and the sensor 575 can all be connected together via interconnects 555, e.g., via patterns metallic traces formed on a substrate material on which the components (e.g., 579, 570, 575) are disposed. Further, the electrodes 560a, 560b could comprise metallic traces or patterns formed on such a substrate material. Alternatively, the components of the ingestible device 550 could be disposed on or within the ingestible device 550 is some other way and electrically connected by some other means (e.g., wires, conductive adhesives). The ingestible device 550 could include an electrochemical battery and/or ultracapacitor to store energy for use by the device 550 and/or the ingestible device 550 could be powered by some other means (e.g., by accessing chemical energy in chyme or other digestive fluids to which the device 550 is exposed).

The actuated drug reservoir 579 could include microfluidic channels, microfluidic reservoirs, electrophoretic elements (e.g., elements configured to apply generate an electrical field to control to flow or motion of a charged drug or a charged drug carrier), electrowetting elements (e.g., elements configured to wet channels of an actuated drug reservoir to control a degree of fluid contact, mass flow, and/or diffusion of a drug between a drug reservoir and tissue or fluids of the body 501), electromechanical and/or microfluidic valves, or other elements that are operable to control a timing and/or amount of drug released from the ingestible device 550.

To facilitate operation in a GI tract of the body 501, the ingestible device 550 could have a spherical shape, a rounded elongate shape, a pill shape, or some other shape specified to facilitate swallowing of the device 550 and transport of the device 550 through the GI tract. The surface of the ingestible device 550 could be smooth and/or could include a layer of a lubricating material. The electrodes 560a, 560b could be disposed on the surface of the ingestible device 550 such that in-body electrical signals can be transmitted between the body-mountable device 510 and the ingestible device 550 when the body-mountable device 510 is mounted to an external body surface such that electrodes of the body-mountable device 510 are in contact with fluid of the body and the ingestible device 550 is located in a GI tract. Note that the ingestible device 550 could include further electrodes (e.g., a plurality of electrodes located at a variety of locations on the surface of the ingestible device 550).

Transmitting in-body electrical signals via electrodes of a device (e.g., via the electrodes 520a, 520b of the body-mountable device or the electrodes 560a, 560b of the ingestible device 550) can include using a transmitter that is coupled to the electrodes to generate the in-body electrical signals. Such a transmitter could be part of a controller (e.g., 530, 570) of the device or could be composed of one or more independent components (e.g., pulse generators, voltage and/or current sources, switches, boost converters, oscillators, clocks, encoders). Such a transmitter could be electrically coupled to the electrodes and operable to generate a time-varying waveform of current and/or voltage that could be applied across and/or through two or more electrodes to generate an in-body electrical signal. The transmitter could operate to apply a plurality of single pulses, biphasic pulses, or other time-varying patterns of electrical current and/or voltage to the electrodes in order to indicate some information. For example, the absolute or relative timing of the generated pulses could encode information. Additionally or alternatively, the polarity of single and/or biphasic pulses could encode information. The transmitter could be coupled to a pair of electrodes or to more than two electrodes. In examples wherein the transmitter is coupled to more than two electrodes, the transmitter could select pairs of electrode through which to transmit in-body electrical signals (e.g., by operating electrical switches to couple a selected pairs of electrodes to the transmitter), could operate the more than two electrodes as a phased array to transmit in-body electrical signals (e.g., to control a direction of propagation of a beam of in-body electrical signals within a body), or could operate the more than two electrodes to transmit in-body electrical signals in some other way.

In some examples, the absolute timing of a transmitted pulse (or other feature of a transmitted in-body electrical signal) could be used to determine information related to the relative location of first and second devices such that a distance between the first and second devices could be determined. In some examples, this could include a first device transmitting a first in-body electrical signal (e.g., the first device could generate a single biphasic pulse) and a second device could, upon receiving the first in-body electrical signal, transmit a second in-body electrical signal (e.g., second first device could generate a single biphasic pulse). The first device could then receive the second in-body electrical signal and determine a distance between the first and second devices (e.g., a distance traveled, through the body, by the first and second in-body electrical signals to propagate between the first and second devices) based on a time difference between the transmission of the first in-body electrical signal and the reception, by the first device, of the second in-body electrical signal (e.g., by dividing the time difference in half and dividing by a propagation velocity of the in-body electrical signals). In another example, the first and second devices could include respective clocks that are synchronized, and the first device could transmit an in-body electrical signal at a pre-specified time and/or the first device could transmit an in-body electrical signal with an indication of the timing of transmission of the in-body electrical signal. The second device could then detect the in-body electrical signal and could determine a distance between the first and second devices based on a time difference between the transmission and reception of the in-body electrical signals. Other methods for using the propagation rate of in-body electrical signals to determine distances between devices on or within a body are anticipated.

Receiving in-body electrical signals via electrodes of a device (e.g., via the electrodes 520a, 520b of the body-mountable device or the electrodes 560a, 560b of the ingestible device 550) can include using a receiver that is coupled to the electrodes to receive the in-body electrical signals. Such a receiver could be part of a controller (e.g., 530, 570) of the device or could be composed of one or more independent components (e.g., amplifiers, filters, pulse-shaping networks, comparators, analog-to digital converters (ADCs), analog correlators, voltage and/or current references, switches, oscillators, clocks, decoders). Such a receiver could be electrically coupled to the electrodes and operable to detect a time-varying waveform of voltage that is present between two or more electrodes to detect an in-body electrical signal. In examples wherein the receiver is coupled to more than two electrodes, the receiver could select pairs of electrodes to use to detect in-body electrical signals (e.g., to maximize a magnitude of a received signal), could operate the more than two electrodes as a phased array to receive in-body electrical signals (e.g., to control a direction from which in-body electrical signals are received relative to a device), or could operate the more than two electrodes to receive in-body electrical signals in some other way.

A receiver could operate in a variety of ways to receive in-body electrical signals. In some examples, this could include operating an ADC to sample the voltage across two or more electrodes at a plurality of points in time. The sampled voltages could then be used to detect the timing, polarity, magnitude or other information about pulses of the in-body signal, a phase, frequency or amplitude of a sinusoid of the in-body signal, or to determine some other information about the in-body electrical signal. The samples could be generated at a regular rate, during specified periods of time (e.g., during periods of time when it is expected that a pulse or other feature of an in-body electrical signal may be received through the electrodes), or according to some other timing or consideration.

In some examples, receiving in-body electrical signals could include detecting the output of a comparator, a pulse-shaping network, an analog comparator, or some other analog components that receive, as input, signals received directly or indirectly from the electrodes used to receive the in-body electrical signals. For example, an analog correlator could be used to detect a time-varying waveform of voltages across such electrodes. The analog correlator could include an amplifier and a plurality of capacitors, and could be operated to, during different periods of time, use the amplifier to charge respective different capacitors of the plurality of capacitors. As a result, the charge in a particular capacitor, when not being charged by the amplifier, could be related to an integral of the voltage across the electrodes during a period of time when the particular capacitor was being charged by the amplifier. A set of voltages across the capacitors could be used to determine a timing of reception of a pulse or other feature of an in-body electrical signal or to determine some other information about in-body electrical signals.

It is noted that the block diagram shown in FIG. 5 is described in connection with functional modules for convenience in description. However, embodiments of the body-mountable device 510 and/or ingestible device 550 can be arranged with one or more of the functional modules ("sub-systems") implemented in a single chip, integrated circuit, and/or physical feature. That is, the functional blocks in FIG. 5 need not be implemented as separated modules. Moreover, one or more of the functional modules described in FIG. 5 can be implemented by separately packaged chips electrically connected to one another. Further, note that a body-mountable device and/or an ingestible device as described herein could include additional or alternative components to those shown in FIG. 5 (e.g., additional sensors, actuated drug reservoirs, electrodes, batteries, controllers, transmitters, receivers, stimulators, etc.). For example, the body-mountable device 510 could lack the communication interface 535 and could be configured to operate independent of any external devices (e.g., 580) to communicate with the ingestible device 550 or other devices on or within the body 501 via in-body electrical signals.

The external device 580 includes a communication interface 588 to send and receive wireless signals to and from the body-mountable device 510. The external device 580 also includes a computing system with a processor 586 in communication with a memory 582. The external device 580 can also include one or more of user controls 585, and a display 587. The memory 582 is a non-transitory computer-readable medium that can include, without limitation, magnetic disks, optical disks, organic memory, and/or any other volatile (e.g.

RAM) or non-volatile (e.g. ROM) storage system readable by the processor 586. The memory 582 can include a data storage 583 to store indications of data, such as sensor readings (e.g., related to readings generated by the sensor 575, transmitted via in-body electrical signals from the ingestible device 550 to the body-mountable device 510, and transmitted via radio frequency or optical signals from the body-mountable device 510 to the external device 580), program settings (e.g., to adjust behavior of the body-mountable device 510, ingestible device 550 and/or external device 580), etc. The memory 582 can also include program instructions 584 for execution by the processor 586 to cause the external device 580 to perform processes specified by the instructions 584. For example, the program instructions 584 can cause external device 580 to perform any of the function described herein. For example, program instructions 584 may cause the external device 580 to provide a user interface that allows for retrieving information communicated from the body-mountable device 510 (e.g., sensor outputs or other information related to the sensor 575) by displaying that information on the display 587 in response to commands input through the user controls 585.

The external device 580 can be a smart phone, digital assistant, or other portable computing device with radios, light emitters, light detectors, or other wireless connectivity sufficient to provide for wireless communication with the communication interface 535 of the body-mountable device 510. The external device 580 can also be implemented as an wireless module (e.g., a radio, an optical data link) that can be plugged into a portable computing device, such as in an example where radio frequency wireless signals used to communicate with the body-mountable device 510 are at carrier frequencies not commonly employed in portable computing devices. In some instances, the external device 580 is a special-purpose device configured to be disposed relatively near a mounting location of the body-mountable device 510 on the wearer's body (e.g., near a wearer's eye) to allow the communication interfaces 535, 588 to operate with a low power budget. The external device 580 could also be implemented in eye glasses or a head-mounted display.

VI. Example Methods

Figure 6:
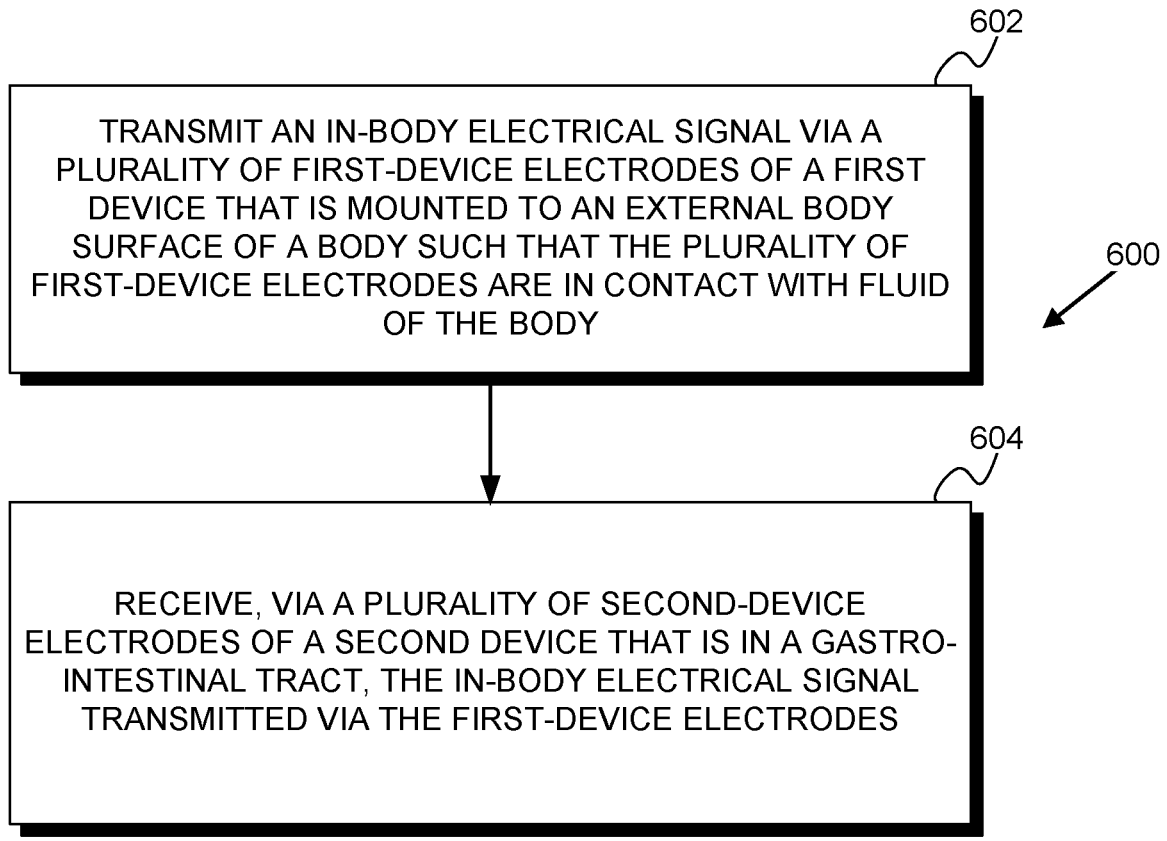
FIG. 6 is a flowchart of an example method.

FIG. 6 is a flowchart of a method 600 for operating a first device and a second device to communicate via in-body electrical signals. The first device includes a plurality of first-device electrodes and is mounted to an external body surface of a body such that that the plurality of first-device electrodes are in contact with fluid of the body. When the first device is so mounted, the plurality of first-device electrodes are operable to transmit and/or receive in-body electrical signals. The second device is located in a gastrointestinal (GI) tract of the body and includes a plurality of second-device electrodes that are operable to transmit and/or receive in-body electrical signals. The first device may be an eye-mountable device and may include a shaped polymeric material (e.g., a hydrogel shaped to form an ophthalmic lens) having a concave surface and a convex surface, where the concave surface is configured to be removably mounted over a corneal surface of an eye and the convex surface is configured to be compatible with eyelid motion when the concave surface is so mounted. The first and second devices could each include one or more sensors, controllers, energy storage elements (e.g., electrochemical batteries) or other elements to facilitate the functions described herein or to facilitate further functionality.

The method 600 includes transmitting an in-body electrical signal via the plurality of first-device electrodes of the first device that is mounted to the external body surface (602). This could include applying a time-varying waveform of current and/or voltage through and/or across two or more electrodes of the plurality of first-device electrodes. Such a time-varying waveform could include single pulses, biphasic pulses, sinusoids, or other features having respective properties specified according to an application, e.g., to encode a message or some other information. Such information could include commands to perform an action (e.g., commands to release a drug, commands to measure a physiological property), programming for another device, operational parameters for another device, timing information (e.g., a timing of a pulse of the in-body electrical signal could be used to synchronize a clock of a receiving device and/or a trigger for a receiving device to responsively emit a further in-body electrical signal to facilitate determination of a distance between the first device and the receiving device), or some other information. Such information could be encoded into the in-body electrical signal via a variety of methods, e.g., according to a pulse-position encoding, a pulse width encoding, a pulse frequency encoding, a frequency modulation of a sinusoid, an amplitude modulation of a sinusoid, or some other method for representing information content in properties of an electrical signal.

The method 600 includes receiving, via the plurality of second-device electrodes of the second device that is in the GI tract, the in-body electrical signal transmitted via the first-device electrodes (604). This could include detecting a time-varying waveform of voltage across two or more electrodes of the plurality of second-device electrodes. Detecting such a time-varying voltage waveform could include operating an ADC to detect the voltage across the electrodes at a plurality of points in time and/or detecting an output of a comparator, amplifier, pulse detector, pulse shaping network, analog correlator, or other analog and/or digital components of the second device. The in-body electrical signal could include a command, an operational parameter, programming, or some other information, and receiving the in-body electrical signal (604) could include decoding the detected signal to determine the information, e.g., to determine that the received in-body electrical signal represented a command to release a drug, to measure a physiological property, or to perform some other action.

The method 600 could include additional steps or elements in addition to those depicted in FIG. 6 (i.e., 602, 604). For example, the method 600 could include operating a sensor of the second device to measure a physiological property of the body (e.g., to detect a pH, to detect the concentration of an analyte, to generate an image of the tissues or contents of the GI tract). Such a measurement could be performed in response to receiving an in-body electrical signal that includes a command to perform the measurement. The method 600 could further include transmitting, from the second device, a second in-body electrical signal to indicate such a measured physiological property and receiving, by the first device, such a second in-body electrical signal. The method 600 could further include the first device communicating, via radio frequency signals, optical signals, or some other wireless signals, with an external device. For example, the first device could transmit, to the external device, a wireless indication of a physiological property measured by the second device and transmitted to the first device via in-body electrical signals. In some examples, the method 600 could include the second device receiving a drug release command, via in-body electrical signals, from the first device and the second device responsively operating an actuated drug reservoir to release a drug into the GI tract responsive to receiving the drug release command. The method 600 could include other steps or elements as described elsewhere herein, or some further steps or elements.

VII. Conclusion

Where example embodiments involve information related to a person or devices of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures. Further, note that while example embodiments of eye-mountable devices described in connection with ingestible devices or other devices disposed in a gastro-intestinal tract or disposed in some other location within a body, devices and methods as described herein could be incorporated into other devices or contexts, e.g., devices configured to be disposed within an environment that includes a conductive fluid medium (e.g., saline, or some other aqueous solution, gel, or other aqueous medium that includes dissolved ions) and to communicate, via electrical signals transmitted through the conductive fluid medium, with devices disposed on an external surface of the conductive fluid medium, e.g., to facilitate communication between the devices within the environment and external devices that are outside of the environment and that are configured to communicate with the devices disposed on the external surface of the environment. Such an environment could include an aqueous fluid of an animal body (e.g., a first device mounted to an eye surface and a second device located within a body cavity or tissue, or other location within the animal body), a natural environment (e.g., a lake, stream, river, marsh, or other environment wherein a first device could be disposed on an external surface of a conductive fluid medium of the body and a second device could be disposed within such a medium), or some other environment.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
a first device, wherein the first device is mountable on an external body surface of a body and comprises:
a plurality of first-device electrodes, wherein the first device is an eye-mountable device that can be mounted on a surface of an eye of the body such that the plurality of first-device electrodes are in contact with tear fluid of the eye; and
a first-device transmitter coupled to the plurality of first-device electrodes, wherein the first-device transmitter is operable to transmit an in-body electrical signal via the first-device electrodes; and
a second device, wherein the second device is operable in the body and comprises:
a plurality of second-device electrodes; and
a second-device receiver coupled to the plurality of second-device electrodes, wherein the second-device receiver is operable to receive, via the second-device electrodes, the in-body electrical signal transmitted by the first-device transmitter via propagation of the in-body electrical signal through the body when the second device is in the body and the first device is mounted on the surface of the eye such that the plurality of first-device electrodes are in contact with tear fluid of the eye.

2. The system of claim 1, wherein the second device further comprises:
a sensor operable to detect a property of the body; and
a second-device transmitter coupled to the plurality of second-device electrodes, wherein the second-device transmitter is operable to transmit an in-body electrical signal via the second-device electrodes, wherein the in-body electrical signal transmitted by the second-device transmitter provides an indication of the property detected by the sensor, and wherein the first device further comprises:
a first-device receiver coupled to the plurality of first-device electrodes, wherein the first-device receiver is operable to receive, via the first-device electrodes, the in-body electrical signal transmitted by the second-device transmitter when the second device is in the body and the first device is mounted on the surface of the eye such that the plurality of first-device electrodes are in contact with tear fluid of the eye.

3. The system of claim 1, wherein the second device is an ingestible device that is operable in a gastro-intestinal tract.

4. The system of claim 3, wherein the second device further comprises:
a second-device transmitter that is coupled to the plurality of second-device electrodes, wherein the second-device transmitter is operable to transmit an in-body electrical signal via the second-device electrodes in response to the second-device receiver receiving the in-body electrical signal transmitted by the first-device transmitter, and wherein the first device further comprises:
a first-device receiver coupled to the plurality of first-device electrodes, wherein the first-device receiver is operable to receive, via the first-device electrodes, the in-body electrical signal transmitted by the second-device transmitter when the second device is in the body and the first device is mounted on the surface of the eye such that the plurality of first-device electrodes are in contact with tear fluid of the eye; and
a controller coupled to the first-device transmitter and the first-device receiver, wherein the controller is configured to determine a distance between the first device and the second device based on a relative timing of the first-device transmitter transmitting an in-body electrical signal to the second device and the first-device receiver receiving an in-body electrical signal from the second device.

5. The system of claim 1, wherein the first device is an eye-mountable device that can be mounted on the surface of the eye of the body such that the plurality of first-device electrodes are in contact with tear fluid of the eye.

6. The system of claim 5, wherein the first device further comprises:
a sensor operable to detect a command gesture that comprises at least one of an eye movement or an eyelid movement, wherein the in-body electrical signal transmitted by the first-device transmitter provides a drug release command in response to the sensor detecting the command gesture, wherein the second device further comprises:
an actuated drug reservoir that contains a drug, wherein the actuated drug reservoir is operable to release an amount of the drug in response to the second-device receiver receiving an in-body electrical signal that includes the drug release command.

7. A body-mountable device, wherein the body-mountable device comprises:
a plurality of electrodes, wherein the body-mountable device is an eye-mountable device that can be mounted on a surface of an eye of the body such that the plurality of electrodes are in contact with tear fluid of the eye; and
a transmitter coupled to the plurality of electrodes, wherein the transmitter is operable to transmit an in-body electrical signal via the electrodes, wherein the transmitted in-body electrical signal propagates through the body to be received by a second device when the second device is in the body and the body-mountable device is mounted on the surface of the eye such that the plurality of electrodes are in contact with tear fluid of the eye; and
a receiver coupled to the plurality of electrodes, wherein the receiver is operable to receive, via the electrodes, the in-body electrical signal that is transmitted by the second device when the second device is in the body and the body-mountable device is mounted on the surface of the eye such that the plurality of electrodes are in contact with tear fluid of the eye, wherein the in-body electrical signal transmitted by the second device provides an indication of a property of the body detected by the second device.

8. The body-mountable device of claim 7, wherein the in-body electrical signal transmitted by the second device provides an indication of an image of an interior volume of the body.

9. The body-mountable device of claim 7, further comprising:
a user interface, wherein the user interface is operable to provide an indication to a wearer when the body-mountable device is mounted on the surface of the eye such that the plurality of electrodes are in contact with tear fluid of the eye; and
a controller coupled to the user interface and the receiver, wherein the controller is configured to provide the indication to a wearer, using the user interface, based on a signal received using the receiver.

10. The body-mountable device of claim 7, wherein the body-mountable device further comprises:
a controller coupled to the transmitter and the receiver, wherein the controller is configured to determine a distance between the body-mountable device and the second device based on a relative timing of the transmitter transmitting an in-body electrical signal to the second device and the receiver receiving an in-body electrical signal from the second device.

11. The body-mountable device of claim 7, wherein the body-mountable device further comprises:
a sensor operable to detect a command gesture that comprises at least one of an eye movement or an eyelid movement, wherein the in-body electrical signal transmitted by the transmitter provides a drug release command in response to the sensor detecting the command gesture.

12. The body-mountable device of claim 7, wherein the in-body electrical signal received by the receiver provides an indication of a property of a gastro-intestinal tract of the body.

13. A method comprising:
transmitting an in-body electrical signal via a plurality of first-device electrodes of a first device, wherein the first device is mounted on a surface of an eye of the body such that the plurality of electrodes are in contact with tear fluid of the eye; and
receiving, via a plurality of second-device electrodes of a second device that is in the body, the in-body electrical signal that is transmitted via the first-device electrodes and that propagates through the body to the plurality of second-device electrodes.

14. The method of claim 13, further comprising:
detecting, using a sensor of the second device, a property of the body;
transmitting an in-body electrical signal via the second-device electrodes, wherein the in-body electrical signal transmitted via the second-device electrodes provides an indication of the detected property of the body; and
receiving, via the first-device electrodes, the in-body electrical signal transmitted via the second-device electrodes when the second device is in the body and the first device is mounted on a surface of an eye of the body such the plurality of electrodes are in contact with tear fluid of the eye.

15. The method of claim 14, further comprising:
providing to an external device, using a communication interface of the first device, an indication of the detected property of the body, wherein providing an indication to the external device using the communication interface comprises transmitting, using the communication interface, radio frequency signals or optical signals.

16. The method of claim 13, wherein the first device is mounted on the surface of the eye such that the plurality of electrodes are in contact with tear fluid of the eye.

17. The method of claim 13, further comprising:
transmitting an in-body electrical signal via the second-device electrodes in response to the receiving, via the second-device electrodes, the in-body electrical signal transmitted via the first-device electrodes;
receiving, via the first-device electrodes, the in-body electrical signal transmitted via the second-device electrodes; and
determining a distance between the first device and the second device based on a relative timing of transmitting the in-body electrical signal via a the first-device electrodes and receiving, via the first-device electrodes, the in-body electrical signal transmitted via the second-device electrodes.

18. The method of claim 17, further comprising:
determining that the determined distance between the first device and the second device is within a specified range of distances;
responsive to determining that the determined distance is within the specified range of distances, transmitting a further in-body electrical signal via the first-device electrodes, wherein transmitting the further in-body electrical signal via the first-device electrodes provides a drug release command;
receiving, via the second-device electrodes, the further in-body electrical signal transmitted via the first-device electrodes; and
responsive to receiving, via the second-device electrodes, the further in-body electrical signal providing the drug release command, releasing an amount of a drug from an actuated drug reservoir of the second device.

19. The method of claim 13, wherein transmitting an in-body electrical signal via the first-device electrodes provides a drug release command, and further comprising:
responsive to receiving, via the second-device electrodes, the in-body electrical signal providing the drug release command, releasing an amount of a drug from an actuated drug reservoir of the second device.

* * * * *